(12) United States Patent
Badylak et al.

(10) Patent No.: US 10,729,813 B2
(45) Date of Patent: *Aug. 4, 2020

(54) EXTRACELLULAR MATRIX-DERIVED GELS AND RELATED METHODS

(71) Applicant: University of Pittsburgh—of the Commonwealth System of Higher Education, Pittsburgh, PA (US)

(72) Inventors: Stephen F. Badylak, West Lafayette, IN (US); Donald Freytes, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/593,232

(22) Filed: Oct. 4, 2019

(65) Prior Publication Data

US 2020/0030493 A1 Jan. 30, 2020

Related U.S. Application Data

(60) Continuation of application No. 16/288,831, filed on Feb. 28, 2019, which is a continuation of application No. 15/996,916, filed on Jun. 4, 2018, which is a continuation of application No. 14/182,791, filed on Feb. 18, 2014, now Pat. No. 10,004,827, which is a division of application No. 13/684,830, filed on Nov. 26, 2012, now Pat. No. 8,691,276, which is a continuation of application No. 12/040,140, filed on Feb. 29, 2008, now Pat. No. 8,361,503.

(60) Provisional application No. 60/892,699, filed on Mar. 2, 2007.

(51) Int. Cl.
| | |
|---|---|
| *A61L 27/36* | (2006.01) |
| *C12P 21/06* | (2006.01) |
| *A61L 27/52* | (2006.01) |
| *A61K 35/12* | (2015.01) |
| *A61L 27/34* | (2006.01) |
| *A61L 27/38* | (2006.01) |
| *A61L 27/54* | (2006.01) |
| *A61K 38/00* | (2006.01) |

(52) U.S. Cl.
CPC .......... *A61L 27/3633* (2013.01); *A61K 35/12* (2013.01); *A61L 27/34* (2013.01); *A61L 27/3687* (2013.01); *A61L 27/38* (2013.01); *A61L 27/52* (2013.01); *A61L 27/54* (2013.01); *C12P 21/06* (2013.01); *A61K 38/00* (2013.01); *A61L 2300/64* (2013.01); *A61L 2400/06* (2013.01); *A61L 2420/04* (2013.01)

(58) Field of Classification Search
CPC .. A61L 27/3633; A61L 27/3687; A61L 27/54; A61L 27/52; A61L 27/38; A61L 27/34; A61L 2420/04; A61L 2400/06; A61L 2300/64; C12P 21/06; A61K 35/12; A61K 38/00
See application file for complete search history.

(56) References Cited

U.S. PATENT DOCUMENTS

| | | |
|---|---|---|
| 3,155,095 A | 11/1964 | Brown |
| 4,563,350 A | 1/1986 | Nathan et al. |
| 4,582,640 A | 4/1986 | Smestad et al. |
| 4,902,508 A | 2/1990 | Badylak et al. |
| 4,956,178 A | 9/1990 | Badylak et al. |
| 4,970,298 A | 11/1990 | Silver et al. |
| 5,171,262 A | 12/1992 | MacGregor |
| 5,258,042 A | 11/1993 | Mehta |
| 5,275,826 A | 1/1994 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,516,533 A | 5/1996 | Badylak et al. |
| 5,554,389 A | 9/1996 | Badylak et al. |
| 5,573,784 A | 11/1996 | Badylak et al. |
| 5,645,860 A | 7/1997 | Knapp, Jr. et al. |
| 5,658,594 A | 8/1997 | Al-Hassan |
| 5,665,391 A | 9/1997 | Lea |
| 5,711,969 A | 1/1998 | Patel et al. |
| 5,741,701 A | 4/1998 | Swiderek et al. |
| 5,753,267 A | 5/1998 | Badylak et al. |
| 5,762,966 A | 6/1998 | Knapp, Jr. et al. |
| 5,866,414 A | 2/1999 | Badylak et al. |
| 5,885,619 A | 3/1999 | Patel et al. |

(Continued)

FOREIGN PATENT DOCUMENTS

| | | |
|---|---|---|
| EP | 3000472 B1 | 4/2017 |
| WO | 2005020847 A2 | 3/2005 |

(Continued)

OTHER PUBLICATIONS

Ringel et al., "The application of tissue engineering procedures to repair the larynx." J Speech Lang Hear Res. Feb. 2006, pp. 194-208, vol. 49, No. 1.

(Continued)

*Primary Examiner* — Taeyoon Kim
(74) *Attorney, Agent, or Firm* — The Webb Law Firm

(57) ABSTRACT

Provided are methods for preparing gelled, solubilized extracellular matrix (ECM) compositions useful as cell growth scaffolds. Also provided are compositions prepared according to the methods as well as uses for the compositions. In one embodiment a device, such as a prosthesis, is provided which comprises an inorganic matrix into which the gelled, solubilized ECM is dispersed to facilitate ingrowth of cells into the ECM and thus adaptation and/or attachment of the device to a patient.

25 Claims, 20 Drawing Sheets

(56) References Cited

U.S. PATENT DOCUMENTS

| | | | |
|---|---|---|---|
| 5,955,110 | A | 9/1999 | Patel et al. |
| 5,968,096 | A | 10/1999 | Whitson et al. |
| 6,099,567 | A | 8/2000 | Badylak et al. |
| 6,171,610 | B1 | 1/2001 | Vacanti et al. |
| 6,187,039 | B1 | 2/2001 | Hiles et al. |
| 6,241,981 | B1 | 6/2001 | Cobb et al. |
| 6,264,992 | B1 | 7/2001 | Voytik-Harbin et al. |
| 6,291,240 | B1 | 9/2001 | Mansbridge et al. |
| 6,444,229 | B2 | 9/2002 | Voytik-Harbin et al. |
| 6,448,076 | B2 | 9/2002 | Dennis et al. |
| 6,485,723 | B1 | 11/2002 | Badylak et al. |
| 6,551,618 | B2 | 4/2003 | Baird et al. |
| 6,554,857 | B1 | 4/2003 | Zilla et al. |
| 6,576,265 | B1 | 6/2003 | Spievack |
| 6,579,538 | B1 | 6/2003 | Spievack |
| 6,696,270 | B2 | 2/2004 | Badylak et al. |
| 6,777,231 | B1 | 8/2004 | Katz et al. |
| 6,783,776 | B2 | 8/2004 | Spievack |
| 6,793,939 | B2 | 9/2004 | Badylak |
| 6,849,273 | B2 | 2/2005 | Spievack |
| 6,852,339 | B2 | 2/2005 | Spievack |
| 6,861,074 | B2 | 3/2005 | Spievack |
| 6,887,495 | B2 | 5/2005 | Spievack |
| 6,890,562 | B2 | 5/2005 | Spievack |
| 6,890,563 | B2 | 5/2005 | Spievack |
| 6,890,564 | B2 | 5/2005 | Spievack |
| 6,893,666 | B2 | 5/2005 | Spievack |
| 6,962,814 | B2 | 11/2005 | Mitchell et al. |
| 7,235,295 | B2 | 6/2007 | Laurencin et al. |
| 7,326,571 | B2 | 2/2008 | Freyman |
| 7,402,319 | B2 | 7/2008 | Schmidt et al. |
| 7,851,189 | B2 | 12/2010 | Freyman et al. |
| 8,021,692 | B2 | 9/2011 | Hiles et al. |
| 8,192,763 | B2 | 6/2012 | Johnson |
| 8,241,908 | B2 | 8/2012 | Qian et al. |
| 8,361,503 | B2 | 1/2013 | Badylak et al. |
| 8,465,771 | B2 | 6/2013 | Wan et al. |
| 8,535,719 | B2 | 9/2013 | Badylak et al. |
| 8,691,276 | B2 | 4/2014 | Badylak et al. |
| 8,741,352 | B2 | 6/2014 | Hodde et al. |
| 8,802,436 | B1 | 8/2014 | Kentner et al. |
| 8,871,511 | B1 | 10/2014 | Matheny et al. |
| 8,927,003 | B2 | 1/2015 | Badykak et al. |
| 8,940,292 | B2 | 1/2015 | Atala et al. |
| 8,974,542 | B2 | 3/2015 | Fujimoto et al. |
| 9,119,831 | B2 | 9/2015 | Kentner et al. |
| 9,161,952 | B2 | 10/2015 | Matheny et al. |
| 9,216,236 | B2 | 12/2015 | Machluf et al. |
| 9,238,091 | B2 | 1/2016 | Kentner et al. |
| 9,474,829 | B2 | 10/2016 | Kentner et al. |
| 9,795,713 | B2 | 10/2017 | Kentner et al. |
| 10,004,827 | B2 | 6/2018 | Badylak et al. |
| 2001/0014475 | A1 | 8/2001 | Frondoza et al. |
| 2002/0085994 | A1 | 7/2002 | Ceres et al. |
| 2002/0090725 | A1 | 7/2002 | Simpson et al. |
| 2002/0115208 | A1 | 8/2002 | Mitchell et al. |
| 2003/0012822 | A1 | 1/2003 | Voytik-Harbin et al. |
| 2003/0036797 | A1 | 2/2003 | Malaviya et al. |
| 2003/0036801 | A1 | 2/2003 | Schwartz et al. |
| 2003/0100944 | A1 | 5/2003 | Laksin et al. |
| 2004/0009600 | A1 | 1/2004 | Bowlin et al. |
| 2004/0076657 | A1 | 4/2004 | Wolfinbarger, Jr. et al. |
| 2005/0013870 | A1 | 1/2005 | Freyman et al. |
| 2005/0013872 | A1 | 1/2005 | Freyman |
| 2005/0181016 | A1 | 8/2005 | Freyman et al. |
| 2006/0134079 | A1 | 6/2006 | Sih et al. |
| 2006/0136028 | A1 | 6/2006 | Ross et al. |
| 2006/0147433 | A1 | 7/2006 | Hiles |
| 2006/0149309 | A1 | 7/2006 | Paul et al. |
| 2006/0153815 | A1 | 7/2006 | Seyda et al. |
| 2006/0201996 | A1 | 9/2006 | Hodde |
| 2007/0014755 | A1 | 1/2007 | Beckman et al. |
| 2007/0014773 | A1 | 1/2007 | Matheny et al. |
| 2007/0014870 | A1 | 1/2007 | Matheny |
| 2007/0014871 | A1 | 1/2007 | Matheny |
| 2007/0014872 | A1 | 1/2007 | Matheny et al. |
| 2007/0014873 | A1 | 1/2007 | Matheny |
| 2007/0014874 | A1 | 1/2007 | Matheny |
| 2007/0082060 | A1 | 4/2007 | Hiles et al. |
| 2008/0069852 | A1 | 3/2008 | Shimp et al. |
| 2008/0107750 | A1 | 5/2008 | Hodde et al. |
| 2008/0260831 | A1 | 10/2008 | Badylak et al. |
| 2008/0268019 | A1 | 10/2008 | Badylak et al. |
| 2008/0312340 | A1 | 12/2008 | Hobson et al. |
| 2009/0163990 | A1 | 6/2009 | Yang et al. |
| 2009/0204228 | A1 | 8/2009 | Hiles |
| 2010/0047305 | A1 | 2/2010 | Naughton et al. |
| 2010/0196480 | A1 | 8/2010 | Hiles et al. |
| 2011/0195052 | A1 | 8/2011 | Behnam et al. |
| 2011/0224484 | A1 | 9/2011 | Case et al. |
| 2018/0043057 | A1 | 2/2018 | Kentner et al. |

FOREIGN PATENT DOCUMENTS

| | | |
|---|---|---|
| WO | 2008146956 A1 | 12/2008 |
| WO | 2017008035 A1 | 1/2017 |
| WO | 2017024193 A1 | 2/2017 |

OTHER PUBLICATIONS

Robinson, "Roles for Ca2+, Mg2+ and NaCl in modulating the self-association reaction of hyalin, a major protein component of the sea-urchin extraembryonic hyaline layer", Biochem J. Nov. 15, 1988, pp. 225-228, vol. 256, No. 1.

Robinson et al., "Extracellular matrix scaffold for cardiac repair", Circulation, Aug. 30, 2005, pp. 135-143, vol. 112.

Sacks, "Biaxial mechanical evaluation of planar biological materials", J Elasticity, 2000, pp. 199-246, vol. 61, Nos. 1-3.

Santucci et al., "Resorbable extracellular matrix grafts in urologic reconstruction", Int Braz J Urol., May-Jun. 2005, pp. 192-203, vol. 31, No. 3.

Sarikaya et al., "Antimicrobial activity associated with extracellular matrices", Tissue Eng., Feb. 2002, pp. 53-71, vol. 8, No. 1.

Stankus et al., "Microintegrating smooth muscle cells into a biodegradable, elastomeric fiber matrix", Biomaterials, Feb. 2006, pp. 735-744, vol. 27, No. 5.

Stankus et al., "Fabrication of biodegradable elastomeric scaffolds with sub-micron morphologies." J Biomed Mater Res A., Sep. 15, 2004, pp. 603-614, vol. 70, No. 4.

Stankus et al. "Fabrication of cell microintegrated blood vessel constructs through electrohydrodynamic atomization." Biomaterials., Jun. 2007, pp. 2738-2746, vol. 28, No. 17.

Suwiwat et al., Clin Cancer Res., Apr. 1, 2004, pp. 2491-2498, vol. 10.

Temple et al., Electrostatic transportation of living cells through air, Abstracts of Papers, 223 ACS National Meeting, Apr. 7-11, 2002.

Veazey et al., "Mammalian cell delivery via aerosol deposition." J Biomed Mater Res B Appl Biomater., Feb. 15, 2005, pp. 334-338, vol. 72, No. 2.

Venere, "New materials hold promise for human healing applications," Purdue News, Mar. 22, 2001.

Williams et al., "Collagen fibril formation. Optimal in vitro conditions and preliminary kinetic results", J Biol Chem., Sep. 25, 1978, pp. 6578-6585, vol. 253, No. 18.

Wood et al., "Use of a particulate extracellular matrix bioscaffold for treatment of acquired urinary incontinence in dogs." J Am Vet Med Assoc., Apr. 1, 2005, pp. 1095-1097, vol. 226, No. 7.

Wright Medical Technology, Comparative analysis: GRAFT JACKET™ Periosteum Replacement Scaffold & SIS™ Porcine Small Intestine Submucosa, Copyright in 2002.

Xu et al., "Aligned biodegradable nanofibrous structure: a potential scaffold for blood vessel engineering", Biomaterials, Feb. 2004, pp. 877-886, vol. 25, No. 5.

Xu et al., "Injectable tissue-engineered cartilage with different chondrocyte sources", Plast Reconstr Surg., Apr. 15, 2004, pp. 1361-1371, vol. 113, No. 5.

Zantop et al., "Extracellular matrix scaffolds are repopulated, in part, by bone marrow-derived cells in a mouse model of achilles tendon reconstruction", J Orthop Res., Jun. 2006, pp. 1299-1309, vol. 24, No. 6.

(56) References Cited

OTHER PUBLICATIONS

Zhang et al., "Artificial matrix helps neonatal cardiomyocytes restore injured myocardium in rats", Artif Organs, Feb. 2006, pp. 86-93, vol. 30, No. 2.
Badylak et al., "Resorbable bioscaffold for esophageal repair in a dog model", J Pediatr Surg., Jul. 2000, pp. 1097-1103, vol. 35, No. 7.
Badylak et al., "Esophageal reconstruction with ECM and muscle tissue in a dog model", J Surg Res., Sep. 2005, pp. 87-97, vol. 128, No. 1.
Badylak et al., "The use of extracellular matrix as an inductive scaffold for the partial replacement of functional myocardium", Cell Transplant , 2006, pp. 29-40.
Badylak et al., "Naturally occurring extracellular matrix as a scaffold for musculoskeletal repair", CLin Orthop Relat Res., Oct. 1999, pp. 333-343.
Badylak et al., "The use of xenogenic small intestinal submucosa as a biomaterial for Achilles tendon repair in a dog model", J Biomed Mater Res., Aug. 1995, pp. 977-985, vol. 29, No. 8.
Badylak et al., "Extracellular matrix for myocardial repair", Heart Surg Forum, 2003, pp. 20-26, vol. 6, No. 2.
Badylak et al., "Xenogenic extracellular matrix as a scaffold for tissue reconstruction", Transpl Immunol, 2004, pp. 367-377, vol. 12.
Badylak et al., "The extracellular matrix as a scaffold for tissue reconstruction", Seminars in Cell & Developmental Biology, 2002, pp. 377-383, vol. 13.
Bernacca et al., "Polyurethane heart valve durability: effects of leaflet thickness and material", Int J Artif Organs., Jun. 1997, pp. 327-331, vol. 20, No. 6.
Billiar et al., "Biaxial mechanical properties of the natural and glutaraldehyde treated aortic valve cusp—Part I: Experimental results", J Biomech Eng., Feb. 2000, pp. 23-30, vol. 122, No. 1.
Brightman et al., "Time-Lapse Confocal Reflection Microscopy of Collagen Fibrillogenesis and Extracellular Matrix Assembly In Vitro". Biopolymers. Sep. 2000, pp. 222-234, vol. 54, No. 3.
Chaudhuri et al., "Detection and gradation of oriented texture", Pattern Recogn Lett., 1993, pp. 147-153, vol. 14, No. 2.
Courtney et al., "Meso- and micromechanics of elastomeric electrospun PEUU scaffolds for cardiovascular tissue engineering, Regenerate World Congress on Tissue Engineering and Regenerative Medicine", Apr. 25-27, 2006, Abstract # 572.
Courtney et al., "Micromechanics of electrospun polyester urethane urea scaffolds." Society for Biomaterials 2006 Annual Meeting, Apr. 26-29, 2006, vol. XXIX, Abstract # 163.
Courtney et al., "Micromechanics of electrospun poly ester urethane urea scaffolds for soft tissue engineering." Fifth World Congress of Biomechanics, Jul. 29-Aug. 4, 2006, p. 262.
Courtney et al., "Incorporation of fiber tortuosity effects in a constitutive model for scaffolds." ASME 2006 Summer Bioengineering Conference, Jun. 21-25, 2006, Abstract # BI02005-157686.
Courtney et al., "Design and analysis of tissue engineering scaffolds that mimic soft tissue mechanical anisotropy", Biomaterials, Jul. 2006, pp. 3631-3638, vol. 27, No. 19.
Courtney et al., "Analysis and design of novel electrospun PEUU scaffolds for soft tissue engineering", The 8th Annual Meeting of the Tissue Engineering Society International, Oct. 22-25, 2005, Abstract # 193.
Courtney et al., "Analysis and design of novel electrospun PEUU scaffolds for soft tissue engineering", ASME 2005 Summer Bioengineering Conference, Jun. 22-26, 2005, Abstract # b0241329.
Courtney et al., "Structural and mechanical characterization of poly (ester urethane) elastomeric scaffolds for cardiovascular soft tissue engineering", Society for Biomaterials 30th Annual Meeting, Apr. 27-30, 2005.
Courtney et al., "Analysis and design of novel electrospun PEUU scaffolds for soft tissue engineering", 2005 Annual Fall Mtg, Nov. 28-Dec. 1, 2005, Abstract L 13.1.
Dedecker et al., "Small intestinal submucosa (SIS): prospects in urogenital surgery", Prog Urol., Jun. 2005, vol. 1 No. 3, pp. 405-410, (English-language Abstract included).
Deglau et al., "Surface modification of vascular tissue for targeted delivery of endothelial cells and microspheres", Abstract for Biomedical Engineering Society 2000 Annual Fall Meeting, Oct. 12-14, 2000, vol. 28 (Supplement): p. 23.
Dejardin et al., "Tissue-engineered rotator cuff tendon using porcine small intestine submucosa, Histologic and mechanical evaluation in dogs", AJSM, 2001, pp. 175-184, No. 29.
De La Fuente et al., "Evaluation of porcine-derived small intestine submucosa as a biodegradable graft for gastrointestinal healing", J Gastrointest Surg. 2003, pp. 96-101 No. 7.
Duruisseau et al., "Endoscopic rehabilitation of vocal cord paralysis with a silicone elastomer suspension implant", Otolaryngol Head Neck Surg. Sep. 2004, pp. 241-247, vol. 131 No. 3.
Freytes et al., "Biaxial strength of multilaminated extracellular matrix scaffolds", Biomaterials, 2004, pp. 2353-2361 vol. 25, No. 12.
Freytes et al., "Porcine Urinary Bladder Matrix Derived Gel for Tissue Engineering Applications", Regenerate World Congress and Society for Biomaterials, 2006.
Frisk et al., Electrophoresis, 2005, pp. 4751-4758, vol. 26.
Gelman et al., "Collagen fibril formation. Evidence for a multistep process", J Biol Chem. Jan. 10, 1979, pp. 180-186, vol. 254, No. 1.
Gilbert et al., "Development of a Hybrid ECM/Porous Metal Scaffold for Connective Tissue Ingrowth", Regenerate World Congress Meeting, Apr. 2006.
Grashow et al., "Biaxial stress-stretch behavior of the mitral valve anterior leaflet at physiologic strain rates." Ann Biomed Eng., Feb. 2006, pp. 315-325, vol. 34, No. 2.
Guan et al., "Preparation and characterization of highly porous, biodegradable polyurethane scaffolds for soft tissue applications", Biomaterials, Jun. 2005, pp. 3961-3971, vol. 26, No. 18.
Guan et al., "Biodegradable poly (ether ester urethane) urea elastomers based on poly (ether ester) triblock copolymers and putrescine: synthesis, characterization and cytocompatibility", Biomaterials, Jan. 2004, pp. 85-96, vol. 25, No. 1.
Guan et al., "Synthesis, characterization and cytocompatibility of polyurethaneurea elastomers with designed elastase sensitivity", Biomacromolecules, Sep.-Oct. 2005, pp. 2833-2842, vol. 6 No. 5.
Hacking et al., "Fibrous tissue ingrowth and attachment to porous tantalum", J Biomed Mater Res, 2000, pp. 631-638, No. 52.
Higuera et al., "Tendon reattachment to a metallic implant using an allogenic bone plate augmented with rhOP-1 vs. autogenous cancellous bone and marrow in a canine model." J Orthop Res. Sep. 2005, pp. 1091-1099, vol. 23, No. 5.
Karlon et al., "Automated measurement of myofiber disarray in transgenic mice with ventricular expression of ras." Anat Rec. Dec. 1998, pp. 612-625, vol. 252, No. 4.
Lee et al., "Nanofiber alignment and direction of mechanical strain affect the ECM production of human ACL throblast." Biomaterials, Apr. 2005, pp. 1261-1270, vol. 26, No. 11.
Lehman et al., "Injectable and bulk-forming agents for enhancing the lower esophageal sphincter", Am J Med. Aug. 18, 2003, vol. 115 Suppl 3A:188S-91 S.
Lightner et al., "Injectable agents: present and future", Curr Urol Rep., Oct. 2002, pp. 408-413, vol. 3, No. 5.
Matsuda et al., "Mechanoactive scaffold design of small-diameter artificial graft made of electrospun segmented polyurethane fabrics", J Biomed Mater Res A., Apr. 1, 2005, pp. 125-131, vol. 73, No. 1.
Middleton et al., "Synthetic Biodegradable Polymers as Medical Devices", Medical Plastics and Biomaterials Magazine, Mar. 1998, p. 30.
Nedovic et al., "Cell immobilization by electrostatic droplet generation", Landbauforsch Volk 2002, pp. 11-17, No. 241.
Radisic et al., "Medium perfusion enables engineering of compact and contractile cardiac tissue." Am J Physiol Heart Circ Physiol., Feb. 2004, vol. 286 No. 2.
Ray et al., "Isolation of vascular smooth muscle cells from a single murine aorta", Methods Cell Sci. 2001, pp. 185-188, vol. 23, No. 4.

(56) References Cited

OTHER PUBLICATIONS

Reddy et al., "A simplified method for the analysis of hydroxyproline in biological tissues", Clin Biochem., Jun. 1996, pp. 225-229, vol. 29, No. 3.

Riboldi et al., "Electrospun degradable polyesterurethane membranes: potential scaffolds for skeletal muscle tissue engineering", Biomaterials, Aug. 2005, pp. 4606-4615, vol. 26, No. 22.

Rimsay et al., "Biochemical Analysis of Hyaline Gelation: An Essential Step in the Assembly of the Sea Urchin Extraembryonic Matrix, the Hyaline Layer", Archives of Biochemistry and Biophysics, 2003, pp. 279-286, vol. 414.

Aurora et al., Commercially available extracellular matrix materials for rotator cuff repairs: State of the art and future trends, J Shoulder Elbow Surg, Sep./Oct. 2007, vol. 16, No. 5 Suppl, pp. S171-S178.

Badylak, "The extracellular matrix as a biologic scaffold material", Biomaterials, 2007, vol. 28, pp. 3587-3593.

Badylak et al, "Extracellular matrix as a biological scaffold material: Structure and function", Acta Biomaterialia, 2009, vol. 5, pp. 1-13.

Badylak et al., Host Protection against Deliberate Bacterial Contamination of an Extracellular Matrix Bioscaffold versus Dacron Mesh in a Dog Model of Orthopedic Soft Tissue Repair, J Biomed Mater Res B Appl Biomater, 2003, vol. 67B, pp. 648-654.

Badylak et al., "Immune response to biologic scaffold materials"; Semin Immunol; 2008; pp. 109-116; vol. 20.

Badylak et al.; "Morphologic Study of Small Intestinal Submucosa as a Body Wall Repair Device"; Journal of Surgical Research; 2002; pp. 190-202; vol. 103.

Badylak et al.; "Small Intestinal Submucosa: A Rapidly Resorbed Bioscaffold for Augmentation Cystoplasty in a Dog Model"; Tissue Engineering; 1998; pp. 379-387; vol. 4:4.

Badylak et al, "Small intestinal submucosa: a substrate for in vitro cell growth", J Biomater. Sci. Polym. Edn., 1998, vol. 9(8), pp. 863-878.

Badylak et al, "Small Intestinal Submucosa as a Large Diameter Vascular Graft in the Dog", Journal of Surgical Research, 1989, vol. 47, pp. 74-80.

Badylak et al.; "Strength over Time of a Resorbable Bioscaffold for Body Wall Repair in a Dog Model"; Journal of Surgical Research; 2001; pp. 282-287; vol. 99.

Beattie et al.; "Chemoattraction of progenitor cells by remodeling extracellular matrix scaffolds" Tissue Eng Part A; 2009; pp. 1119-1125; vol. 15.

Brown et al., The basement membrane component of biologic scaffolds derived from extracellular matrix, Tissue Eng., 2006, 519-526, vol. 12, No. 3.

Chen et al.. Acellular collagen matrix as a possible off the shelf biomaterial for urethral repair, Urology, 1999, vol. 54, No. 3, pp. 407-410.

Chen et al.; "Small Bowel Tissue Engineering Using Small Intestinal Submucosa as a Scaffold"; Journal of Surgical Research; 2001; pp. 352-358; vol. 99.

Cobb et al.; "Porcine Small Intestinal Submucosa as a Dural Substitute"; Surg Neurol; 1999; pp. 9-104; vol. 51.

De Long et al.; "Bone grafts and bone graft substitutes in orthopaedic trauma surgery: a critical analysis"; J Bone Joint Burg; 2007; pp. 649-658; vol. 89.

Faulk et al., "ECM hydrogel coating mitigates the chronic inflammatory response to polypropylene mesh", Biomaterials, (2014), p. 8585-8595, 35.

Flynn et al., "Adipose Tissue Engineering with cells in engineered matrices." Organogenesis, 4(4):228-235 (2008).

Flynn et al., Adipose tissue engineering with naturally derived scaffolds and adipose-derived stem cells, Biomater., 28:3834-3842 (2007).

Flynn et al., "Decellularized Placental Matrices for Adipose Tissue Engineering," J. Biomed. Mater. Res. A, 79:359-369 (2006).

Freytes et al.; "Effect of Storage Upon Material Properties of Lyophilized Porcine Extracellular Matrix Derived from the Urinary Bladder"; J Biomed Mater Rs Part B: Appl Biomater 78B; 2006; pp. 327-333.

Freytes et al, "Preparation and rheological characterization of a gel form of the porcine urinary bladder matrix," Biomaterials, 2008, vol. 29, pp. 1630-1637.

Gilbert et al., Decellulariztion of tissues and organs, Biomaterials, 2006, 3675-3683, 27.

Gilbert et al., "Production and characterization of ECM powder: Implications for tissue engineering applications", Biomaterials 2005, vol. 26, pp. 1431-1435.

Gilbert et al.; "Quantification of DNA in biologic scaffold materials"; J Surg Res; 2009; pp. 135-139; vol. 152.

Guo et al., Preparation of the acellular scaffold of the spinal cord and the study of biocompatibility, Spinal Cord, 2010, vol. 48, No. 7, pp. 576-581.

Hiles et al, "Porosity of porcine small-intestinal submucosa for use as a vascular graft", Journal of Biomedical Materials Research, 1993, vol. 27, pp. 139-144.

Hodde et al.; "Effects of sterilization on an extracellular matrix scaffold: Part I. Composition and matrix architecture"; J Mater Sci: Mater Med; 2007; pp. 537-543; vol. 18.

Hodde, Naturally Occurring Scaffolds for Soft Tissue Repair and Regeneration, Tissue Eng, 2002, vol. 8, No. 2, pp. 295-308.

Hodde et al.; "Retention of Endothelial Cell Adherence to Porcine-Derived Extracellular Matrix after Disinfection and Sterilization"; Tissue Engineering; 2002; pp. 225-234; vol. 8:2.

Hodde et al, "Vascular Endothelial Growth Factor in Porcine-Derived Extracellular Matrix", Endothelium, 2001, vol. 8 (1), pp. 11-24.

Jernigan et al., Small Intestinal Submucosa for Vascular Reconstruction in the Presence of Gastrointestinal Contamination, Ann Surg, 2004, vol. 239, No. 5, pp. 733-740.

Neiponice et al., Reinforcement of Esophageal Anastomoses With an Extracellular Matrix Scaffold in a Canine Model, Ann Thorac Surg, 2006, vol. 82, No. 6, pp. 2050-2058.

Prevel et al.; "Small Intestinal Submucosa: Utilization as a Wound Dressing in Full-Thickness Rodent Wounds"; Ann Plast Surg; 1995; pp. 381-388; vol. 35.

Prevel et al.; "Small Intestinal Submucosa: Utilization for Repair of Rodent Abdominal Wall Defects"; Ann Plast Surg 1995; pp. 374-380; vol. 35.

Price et al.. Development of a Decellularized Lung Bioreactor System for Bioengineering the Lung: The Matrix Reloaded, Tissue Eng Part A, 2010, vol. 16, No. 8, pp. 2581-2591.

Schenke-Layland et al.; "Impact of decellularization of xenogeneic tissue on extracellular matrix integrity for tissue engineering of heart valves"; J Struct Biol; 2003; pp. 201-208; vol. 143.

Sellaro et al.; "Maintenance of Hepatic Sinusoidal Endothelial Cell Phenotype In Vitro Using Organ-Specific Extracellular Matrix Scaffolds"; Tissue Engineering; 2007; pp. 2301-2310; vol. 13:9.

Shell et al., Comparison of Small-Intestinal Submucosa and Expanded Polytetraftuoroethylene as a Vascular Conduit in the Presence of Gram-Positive Contamination, Ann Surg, 2005, vol. 241, No. 6, pp. 995-1004.

Shin et al.; "Review: Biomimetic materials for tissue engineering"; Biomalerials; 2003; pp. 4353-4364; vol. 24.

Smith et al, "Improved Growth Factor Directed Vascularization into Fibrin Constructs Through Inclusion of Additional Extracellular Molecules", Microvasc Res., 2007, vol. 73(2), pp. 84-94.

Sondell et al., Regeneration of the rat sciatic nerve into allografts made acellular through chemical extraction, Brain Research, 1998, vol. 795, pp. 44-54.

Stuart et al.; "Influence of chondroitin sulfate on collagen gel structure and mechanical properties at physiologically relevant levels"; Biopolymers; 2008; pp. 841-851; vol. 89.

Valentin et al., Extracellular Matrix Bioscaffolds for Orthopaedic Applications. A Comparative Histologic Study, J Bone Joint Surg Am, 2006, vol. 88, No. 12, pp. 2673-2686.

Van Amerongen et al., The enzymatic degradation of scaffolds and their replacement by vascularized extracellular matrix in the murine myocardium, Biomaterials, 2006, 2247-2257, 27.

(56) References Cited

OTHER PUBLICATIONS

Yang et al.; "Favorable effects of the detergent and enzyme extraction method for preparing decellularized bovine pericardium scaffold for tissue engineered heart valves" J Biomed Mater Res B Appl Biomater; 2009; pp. 354-356; vol. 91.

Yoshida et al.; "Decellularization of bovine anterior cruciate ligament tissues minimizes immunogenic reactions to alpha-gal epitopes by human peripheral blood mononuclear cells"; Knee 2012; pp. 672-675; vol. 19.

Zhang et al.; "Tissue-specific extracellular matrix coatings for the promotion of cell proliferation and maintenance of cell phenotype"; Biomalerials; 2009; pp. 4021-4028; vol. 30.

EXTRACELLULAR MATRIX-DERIVED GELS AND RELATED METHODS

CROSS REFERENCE TO RELATED APPLICATIONS

This application is a continuation of U.S. patent application Ser. No. 16/288,831, filed Feb. 28, 2019, which is a continuation of U.S. patent application Ser. No. 15/996,916, filed Jun. 4, 2018, which is a continuation of U.S. patent application Ser. No. 14/182,791, filed on Feb. 18, 2014 and issued on Jun. 26, 2018, as U.S. Pat. No. 10,004,827, which is a divisional of U.S. patent application Ser. No. 13/684,830, filed on Nov. 26, 2012 and issued on Apr. 8, 2014 as U.S. Pat. No. 8,691,276, which is a continuation of U.S. patent application Ser. No. 12/040,140, filed on Feb. 29, 2008 and issued on Jan. 29, 2013 as U.S. Pat. No. 8,361,503, which claims the benefit under 35 U.S.C. § 119(e) to U.S. Provisional Patent Application No. 60/892,699, filed on Mar. 2, 2007, each of which is incorporated herein by reference in its entirety.

STATEMENT REGARDING FEDERAL FUNDING

This invention was made with government support under Grant No. 5 R01 EB000503-04, awarded by the National Institutes of Health. The government has certain rights in this invention.

BACKGROUND

Extracellular matrix-derived gels, cell-growth scaffolds and related methods are described herein.

The current trend towards minimally invasive, outpatient-based surgical procedures has prompted the development of injectable scaffolds, which can be inductive and bioactive or they can be non-inductive "place holders." Injectable scaffolds can be used in combination with endoscopic or laparoscopic techniques to deliver bioactive proteins and/or cells, or bulking agents to target tissues. Purified collagen, gelatin, autologous fat, hyaluronic acid, and synthetic materials are clinically used as injectable scaffolds in regenerative medicine for the treatment of urinary incontinence, reflux disease, and laryngeal pathologies [Lightner D J, et al. Injectable agents: present and future. Curr Urol Rep. 2002 October; 3(5):408-13; Lehman G A. Injectable and bulk-forming agents for enhancing the lower esophageal sphincter. Am J Med. 2003 Aug. 18; 115 Suppl 3A:188S-91S; Duruisseau O, et al. Endoscopic rehabilitation of vocal cord paralysis with a silicone elastomer suspension implant. Otolaryngol Head Neck Surg. 2004 September; 131(3):241-7]. In addition, purified collagen gels have been investigated in pre-clinical studies as a substrate for the delivery of neonatal cardiomyocytes to infarcted myocardium [Zhang P, et al. Artificial matrix helps neonatal cardiomyocytes restore injured myocardium in rats. Artif Organs. 2006 February; 30(2):86-93] or as an injectable scaffold for articular surface repair [Xu J W, et al. Injectable tissue-engineered cartilage with different chondrocyte sources. Plast Reconstr Surg. 2004 Apr. 15; 113(5):1361-71]. However, overly-purified, chemically modified or synthetic materials can lead to adverse immune responses by the host and limit cell migration into the matrix.

Scaffolds composed of naturally occurring extracellular matrix (ECM) possess many bioactive properties that have been shown to lead to constructive remodeling of virtually every tissue type with minimization of scar tissue formation. ECM-derived scaffolds have been used for the repair of a variety of tissues including lower urinary tract structures [Dedecker F, et al. [Small intestinal submucosa (SIS): prospects in urogenital surgery]. Prog Urol. 2005 June; 15(3):405-10; Wood J D, Simmons-Byrd A, et al. Use of a particulate extracellular matrix bioscaffold for treatment of acquired urinary incontinence in dogs. J Am Vet Med Assoc. 2005 Apr. 1; 226(7):1095-7], esophagus [Badylak S, et al. Resorbable bioscaffold for esophageal repair in a dog model. J Pediatr Surg. 2000 July; 35(7):1097-103; Badylak S F, et al. Esophageal reconstruction with ECM and muscle tissue in a dog model. J Surg Res. 2005 September; 128(1):87-97], cardiac tissue [Badylak S, et al. Extracellular matrix for myocardial repair. Heart Surg Forum. 2003; 6(2):E20-6; Badylak S F, et al. The use of extracellular matrix as an inductive scaffold for the partial replacement of functional myocardium. Cell Transplant. 2006; 15 Suppl 1:S29-40; Robinson K A, et al. Extracellular matrix scaffold for cardiac repair. Circulation. 2005 Aug. 30; 112(9 Suppl):I135-43], and musculotendinous structures [Badylak S, et al. Naturally occurring extracellular matrix as a scaffold for musculoskeletal repair. Clin Orthop Relat Res. 1999 October(367 Suppl):S333-43; Badylak S F, et al. The use of xenogeneic small intestinal submucosa as a biomaterial for Achilles tendon repair in a dog model. J Biomed Mater Res. 1995 August; 29(8):977-85; Zantop T, et al. Extracellular matrix scaffolds are repopulated, in part, by bone marrow-derived cells in a mouse model of achilles tendon reconstruction. J Orthop Res. 2006 June; 24(6):1299-309] tissues, often leading to tissue-specific constructive remodeling without scar formation.

U.S. Pat. No. 5,275,826 discloses an ECM-derived fluidized, injectable, non-immunogenic tissue graft that promotes endogenous tissue growth in the location of the injection of the tissue graft. The composition is comprised of tunica submucosa, muscularis mucosa and stratum compactum of the small intestine of a warm-blooded vertebrate.

U.S. Pat. No. 5,516,533 discloses a tissue graft composition comprised of intestinal submucosa delaminated from both the tunica muscularis (an outer layer of the intestine) and at least the luminal portion of the tunica mucosa (inner layer of the intestine).

U.S. Pat. No. 5,866,414 discloses a cell-growth composition containing protease-digested submucosal tissue, and added nutrients to support cell growth. The submucosal tissue and nutrients are combined in a solution, which is then gelled to form a solid or semi-solid matrix.

U.S. Pat. No. 6,893,666 discloses a composition and methods for using a tissue regenerative matrix to promote the restoration, remodeling or repair of connective tissue. The composition of the matrix comprises devitalized mammalian epithelial basement membrane of the intestine and tunica propria, which can further include submucosa, tunica muscularis, growth factors, a cell, or a polymer. The tissue can be obtained from the urinary bladder, skin, esophagus and small intestine.

U.S. application Ser. No. 11/182,551 discloses a composition consisting essentially of an emulsified or injectable extracellular matrix composition from a mammalian source for regeneration of absent or defective myocardium. The application also discloses a composition comprising synthetic or mammalian extracellular matrix compositions and additional components, such as a cell, peptide, drug, or nutrient. The application also discloses methods of making and using the composition. Divisional applications related to application Ser. No. 11/182,551 include: application Ser. No.

11/367,870; 11/448,351; 11/448,355; 11/448,931; and Ser. No. 11/448,968. These applications disclose a manner of polymerizing the emulsified composition by altering the pH of the composition. However, none of the applications discuss the use of temperature to regulate gelation.

Many forms of ECM scaffolds have already received regulatory approval and have been used in more than 500,000 human patients. However, these current forms of ECM are limited by the material and geometrical properties inherent to the tissue from which they are derived (such as sheets or tubes of tissue) and delivery via injection is limited to powder suspensions.

SUMMARY

Provided are methods for preparing gelled, solubilized extracellular matrix (ECM) compositions useful as cell growth scaffolds. The compositions can be molded prior to implantation or administered to a patient in an un-gelled form prior to gelation where the composition gels in situ. Also provided are compositions prepared according to the methods as well as uses for the compositions. In one embodiment a device, such as a prosthesis, is provided which comprises an inorganic matrix to which the gelled, solubilized ECM is dispersed to facilitate in-growth of cells into the ECM and thus adaptation and/or attachment of the device to a patient.

In one embodiment, injectable ECM-derived gel scaffolds are provided that facilitate delivery of the scaffold via minimally invasive methods while retaining bioactivity. In another embodiment, the gel can be molded into any desired shape for use in a patient, such as a human patient. The gel scaffold can be used for regenerative or augmentative purposes, for example to regenerate organs or tissue in a patient, for example after trauma or surgery to remove tissue, such as a tumor; or for cosmetic purposes, such as enhancement of facial features or breast reconstruction or augmentation. In one embodiment, the gel scaffold is attached to a biocompatible inorganic matrix, such as, without limitation, a matrix of metal fibers or beads.

According to one embodiment, a method of preparing an extracellular matrix-derived gel is provided. The method comprising: (i) comminuting an extracellular matrix, (ii) solubilizing intact, non-dialyzed or non-cross-linked extracellular matrix by digestion with an acid protease in an acidic solution to produce a digest solution, (iii) raising the pH of the digest solution to a pH between 7.2 and 7.8 to produce a neutralized digest solution, and (iv) gelling the solution at a temperature greater than approximately 25° C. The ECM typically is derived from mammalian tissue, such as, without limitation from one of urinary bladder, spleen, liver, heart, pancreas, ovary, or small intestine. In certain embodiments, the ECM is derived from a pig, cow, horse, monkey, or human. In one non-limiting embodiment, the ECM is lyophilized and comminuted. The ECM is then solubilized with an acid protease. The acid protease may be, without limitation, pepsin or trypsin, and in one embodiment is pepsin. The ECM typically is solubilized at an acid pH suitable or optimal for the protease, such as greater than about pH 2, or between pH and 4, for example in a 0.01M HCl solution. The solution typically is solubilized for 12-48 hours, depending upon the tissue type (e.g., see examples below), with mixing (stirring, agitation, admixing, blending, rotating, tilting, etc.).

Once the ECM is solubilized (typically substantially completely) the pH is raised to between 7.2 and 7.8, and according to one embodiment, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution can be gelled at temperatures approaching 37° C., typically at any temperature over 25° C., though gelation proceeds much more rapidly at temperatures over 30° C., and as the temperature approaches physiological temperature. The method typically does not include a dialysis step prior to gelation, yielding a more-complete ECM-like matrix that typically gels at 37° C. more slowly than comparable collagen or dialyzed ECM preparations.

As described herein, the composition can be molded into any shape by any suitable method, including, without limitation, placing into or onto a mold, electrospinning, electrodeposition, injection into a cavity or onto a surface in a patient. Further, a molded gel can be trimmed and otherwise shaped by cutting or other suitable methods. In one non-limiting embodiment, the gel is injected into a site on a patient to add additional bulk or to fill in a void, for example, resulting from trauma or from removal or degradation of tissue. In one non-limiting embodiment, the acidic solubilization solution is mixed in a static mixer with a base and/or buffer during injection into a patient. In further embodiments, cells, drugs, cytokines and/or growth factors can be added to the gel prior to, during or after gelation, so long as the bioactivity of the cells, drugs, cytokines and/or growth factors is not substantially or practically (for the intended use) affected by the processing of the gel to its final form.

Also provided is a novel composition prepared according to one or more processes described above or herein, namely, by a method comprising: (i) comminuting an extracellular matrix, (ii) solubilizing intact, non-dialyzed or non-cross-linked extracellular matrix by digestion with an acid protease in an acidic solution to produce a digest solution, (iii) raising the pH of the digest solution to a pH between 7.2 and 7.8 to produce a neutralized digest solution, and (iv) gelling the solution at a temperature greater than 25° C.

In another embodiment a method of preparing a hybrid extracellular matrix scaffold is provided along with a matrix prepared by that method. A scaffold may be any biocompatible porous, macroporous, microporous, etc. material into which an ECM gel is dispersed or can be dispersed, and which supports the desired bioactivity of the device/scaffold, which is typically cell growth and/or in-growth. The method comprises coating a matrix of a biocompatible scaffold with a solubilized extracellular matrix and gelling the matrix. According to one non-limiting embodiment, the solubilized extracellular matrix can be prepared according to the process of: (i) comminuting an extracellular matrix, (ii) solubilizing intact, non-dialyzed or non-cross-linked extracellular matrix by digestion with an acid protease in an acidic solution to produce a digest solution, and (iii) raising the pH of the digest solution to a pH between 7.2 and 7.8 to produce a neutralized digest solution, and the neutralized digest solution is gelled at a temperature greater than 25° C., including variations of this method described above and herein. In one embodiment, after coating the scaffold, the method further includes ultrasonicating the scaffold. According to non-limiting embodiments, the scaffold comprises one or more of a cobalt-chrome alloy, a stainless steel, titanium, tantalum, and/or a titanium alloy that optionally comprises non-metallic and metallic components. In one non-limiting embodiment, the scaffold comprises a commercial pure titanium. In another, the scaffold comprises a titanium alloy that comprises one or more of molybdenum, tantalum, niobium, zirconium, iron, manganese, chromium, cobalt, nickel, aluminum and lanthanum. The titanium alloy may be an alloy comprising Ti, Al, and V, such as, for example, an alloy comprising about 90% wt. Ti, about 6% wt. Al and about 4% wt. V (Ti6Al4V). In one embodiment, the scaffold comprises filaments. In another, fused beads. The scaffold may comprise an inorganic, calcium-containing mineral, such as, without limitation, apatite, hydroxyapatite or a mineral comprising Ca, P and O. The scaffold also may comprise a polymer (plastic) and/or a ceramic.

In another embodiment, a biocompatible device is provided. The device is coated with a hybrid scaffold comprising gelled solubilized extracellular matrix embedded into a porous scaffold. The device may be, without limitation, a prosthesis or an implant. The prosthesis may be a hand, a forearm, an arm, a foot or a leg prosthesis. In one non-limiting embodiment, the device is a femoral implant for use in a hip-replacement procedure. The gelled solubilized extracellular matrix is, according to one non-limiting embodiment, prepared by a process comprising: (i) comminuting an extracellular matrix, (ii) solubilizing intact, non-dialyzed or non-cross-linked extracellular matrix by digestion with an acid protease in an acidic solution to produce a digest solution, (iii) raising the pH of the digest solution to a pH between 7.2 and 7.8 to produce a neutralized digest solution, and (iv) gelling the solution at a temperature greater than 25° C. in its variations described above and herein.

Lastly, a method of attaching a device to tissue and/or structures of a patient is provided comprising contacting a surface of a device comprising a hybrid inorganic/extracellular matrix scaffold comprising a gelled solubilized extracellular matrix embedded into a porous inorganic scaffold with a patient's cells for a time period sufficient for in-growth of the patient's cells into the scaffold. The surface may be contacted with the cells and the in-growth occurs in vivo and/or ex vivo. Without limitation, the device may be any device, including a prosthesis, as described above or herein. In one embodiment, the gelled solubilized extracellular matrix is prepared by a process comprising: (i) comminuting an extracellular matrix, (ii) solubilizing intact, non-dialyzed or non-cross-linked extracellular matrix by digestion with an acid protease in an acidic solution to produce a digest solution, (iii) raising the pH of the digest solution to a pH between 7.2 and 7.8 to produce a neutralized digest solution, and (iv) gelling the solution at a temperature greater than 25° C.

DETAILED DESCRIPTION

Figure 1:
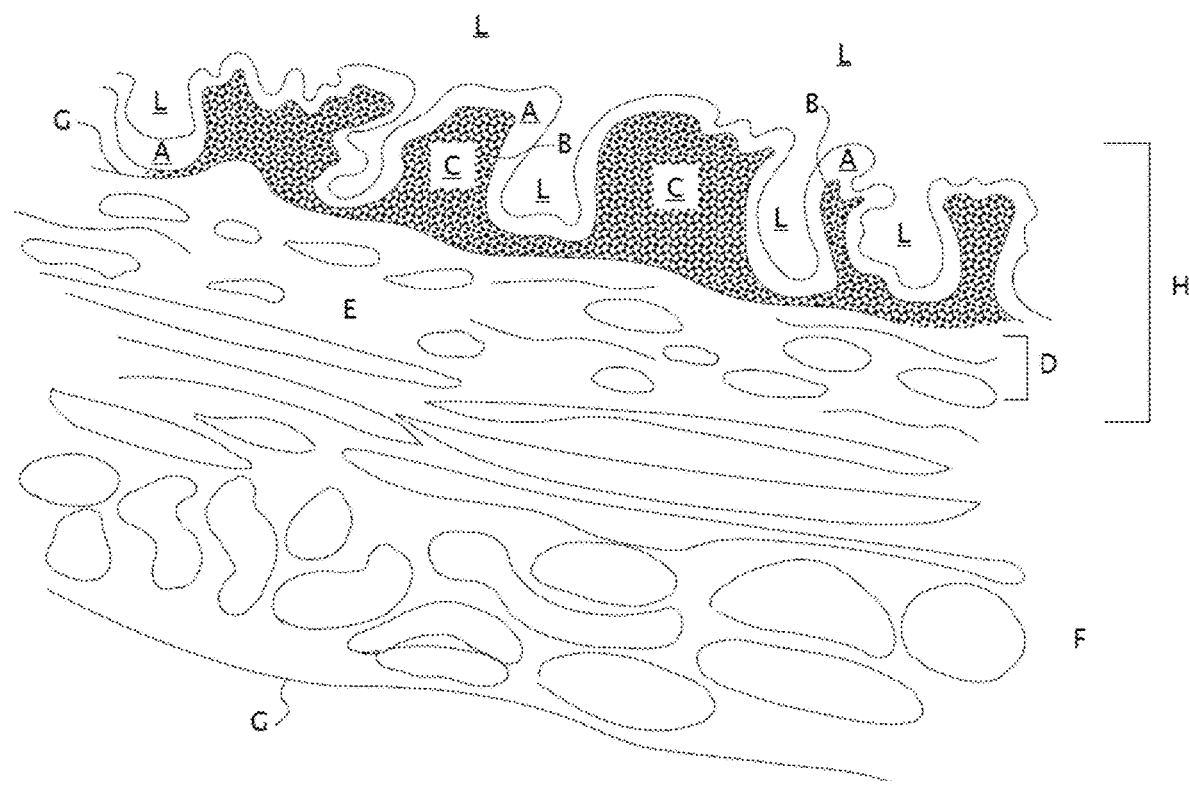
FIG. 1 shows schematically a cross-sectional view of the wall of the urinary bladder (not drawn to scale). The following structures are shown: epithelial cell layer (A), basement membrane (B), tunica propria (C), muscularis mucosa (D), tunica mucosa (E), tunica muscularis externa (F), tunica serosa (G), tunica mucosa (H), and lumen of the bladder (L).

Methods are described herein of preparing an injectable and bioactive extracellular matrix (ECM)-derived composition comprising solubilized extracellular matrix obtained from any of a variety of tissues. Related compositions, devices and methods of use also are described. The viscosity of the matrix increases when warmed to physiological temperatures approaching about 37° C. According to one non-limiting embodiment, the ECM-derived composition is an injectable solution at temperatures lower than 37° C., but a gel at a physiological temperature of 37° C. According to certain embodiments, the gel is bioactive because the entire, intact ECM is solubilized and is not dialyzed, cross-linked and/or otherwise treated to remove or otherwise inactivate ECM structural or functional components, resulting in a highly bioactive gel scaffold that is functionally superior to earlier-described matrices. A general set of principles for preparing an ECM-derived gel is provided along with specific protocols for preparing gels from numerous tissues, including urinary bladder, spleen, liver, heart, pancreas, ovary and small intestine.

The compositions described herein find use as, without limitation, an injectable graft (e.g., xenogeneic, allogeneic or autologous) for tissues, for example, bone or soft tissues, in need of repair or augmentation most typically to correct trauma or disease-induced tissue defects. The compositions also may be used as a filler for implant constructs comprising, for example, a molded construct formed into a desired shape for use in cosmetic or trauma-treating surgical procedures.

The compositions may be implanted into a patient, human or animal, by a number of methods. In one non-limiting embodiment, the compositions are injected as a liquid into a desired site in the patient. The composition may be pre-seeded with cells, and then preferably injected using a larger-bore, e.g. 16 gauge needle, to prevent shearing of cells. In another non-limiting embodiment, the composition is gelled within a mold, and the gelled, molded product is then implanted into the patient at a desired site. The gelled, molded product may be pre-seeded (laid onto the molded gel or mixed in during gelation) with cells, such as cells of the patient.

As used herein, the terms "extracellular matrix" and "ECM" refer to a natural or artificial scaffolding for cell growth. Natural ECMs (ECMs found in multicellular organisms, such as mammals and humans) are complex mixtures of structural and non-structural biomolecules, including, but not limited to, collagens, elastins, laminins, glycosaminoglycans, proteoglycans, antimicrobials, chemoattractants, cytokines, and growth factors. In mammals, ECM often comprises about 90% collagen, in its various forms. The composition and structure of ECMs vary depending on the source of the tissue. For example, small intestine submucosa (SIS), urinary bladder matrix (UBM) and liver stroma ECM each differ in their overall structure and composition due to the unique cellular niche needed for each tissue.

As used herein, the terms "intact extracellular matrix" and "intact ECM" refers to an extracellular matrix that retains activity of its structural and non-structural biomolecules, including, but not limited to, collagens, elastins, laminins, glycosaminoglycans, proteoglycans, antimicrobials, chemoattractants, cytokines, and growth factors, such as, without limitation comminuted ECM as described herein. The activity of the biomolecules within the ECM can be removed chemically or mechanically, for example, by cross-linking and/or by dialyzing the ECM. Intact ECM essentially has not been cross-linked and/or dialyzed, meaning that the ECM has not been subjected to a dialysis and/or a cross-linking process, or conditions other than processes that occur naturally during storage and handling of ECM prior to solubilization, as described herein. Thus, ECM that is substantially cross-linked and/or dialyzed (in anything but a trivial manner which does not substantially affect the gelation and functional characteristics of the ECM in its uses described herein) is not considered to be "intact".

By "Bio Compatible", it is meant that a device, scaffold composition, etc. is essentially, practically (for its intended use) and/or substantially non-toxic, non-injurous or non-inhibiting or non-inhibitory to cells, tissues, organs, and/or organ systems that would come into contact with the device, scaffold, composition, etc.

In general, the method of preparing an ECM-derived gel requires the isolation of ECM from an animal of interest and from a tissue or organ of interest. In certain embodiments, the ECM is isolated from mammalian tissue. As used herein, the term "mammalian tissue" refers to tissue derived from a mammal, wherein tissue comprises any cellular component of an animal. For example and without limitation, tissue can be derived from aggregates of cells, an organ, portions of an organ, combinations of organs. In certain embodiments, the ECM is isolated from a vertebrate animal, for example and without limitation, human, monkey, pig, cattle, and sheep. In certain embodiments, the ECM is isolated from any tissue of an animal, for example and without limitation, urinary bladder, liver, small intestine, esophagus, pancreas, dermis, and heart. In one embodiment, the ECM is derived from a urinary bladder. The ECM may or may not include the basement membrane portion of the ECM. In certain embodiments, the ECM includes at least a portion of the basement membrane. The ECM may or may not retain some of the cellular elements that comprised the original tissue such as capillary endothelial cells or fibrocytes.

As used herein, the term "derive" and any other word forms of cognates thereof, such as, without limitation, "derived" and "derives", refers to a component or components obtained from any stated source by any useful method.

For example and without limitation, an ECM-derived gel refers to a gel comprised of components of ECM obtained from any tissue by any number of methods known in the art for isolating ECM. In another example, mammalian tissue-derived ECM refers to ECM comprised of components of mammalian tissue obtained from a mammal by any useful method.

The ECM can be sterilized by any number of standard techniques, including, but not limited to, exposure to peracetic acid, low dose gamma radiation, gas plasma sterilization, ethylene oxide treatment or electron beam treatment. More typically, sterilization of ECM is obtained by soaking in 0.1% (v/v) peracetic acid, 4% (v/v) ethanol, and 95.9% (v/v) sterile water for two hours. The peracetic acid residue is removed by washing twice for 15 minutes with PBS (pH=7.4) and twice for 15 minutes with sterile water.

Following isolation of the tissue of interest, decellularization is performed by various methods, for example and without limitation, exposure to hypertonic saline, peracetic acid, Triton-X or other detergents. Sterilization and decellularization can be simultaneous. For example and without limitation, sterilization with peracetic acid, described above, also can serve to decellularize the ECM. Decellularized ECM can then be dried, either lyophilized (freeze-dried) or air dried. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state.

As used herein, the term "comminute" and any other word forms or cognates thereof, such as, without limitation, "comminution" and "comminuting", refers to the process of reducing larger particles into smaller particles, including, without limitation, by grinding, blending, shredding, slicing, milling, cutting, shredding. ECM can be comminuted while in any form, including, but not limited to, hydrated forms, frozen, air-dried, lyophilized, powdered, sheet-form.

In order to prepare solubilized ECM tissue, comminuted ECM is digested with an acid protease in an acidic solution to form a digest solution. As used herein, the term "acid protease" refers to an enzyme that cleaves peptide bonds, wherein the enzyme has increased activity of cleaving peptide bonds in an acidic pH. For example and without limitation, acid proteases can include pepsin and trypsin.

The digest solution of ECM typically is kept at a constant stir for a certain amount of time at room temperature. The ECM digest can be used immediately or be stored at −20° C. or frozen at, for example and without limitation, −20° C. or −80° C. To form a "pre-gel" solution, the pH of the digest solution is raised to a pH between 7.2 and 7.8. The pH can be raised by adding one or more of a base or an isotonic buffered solution, for example and without limitation, NaOH or PBS at pH 7.4. The method typically does not include a dialysis step prior to gelation, yielding a more-complete ECM-like matrix that typically gels at 37° C. more slowly than comparable collagen or dialyzed ECM preparations. The gel is therefore is more amenable to injection into a patient, and also retains more of the qualities of native ECM due to retention of many native soluble factors, such as, without limitation, cytokines. The ability of non-dialyzed (whole ECM) preparations prepared from a variety of tissues to gel with kinetics suitable for use in molds or in situ is unexpected.

As used herein, the term "isotonic buffered solution" refers to a solution that is buffered to a pH between 7.2 and 7.8 and that has a balanced concentration of salts to promote an isotonic environment. As used herein, the term "base" refers to any compound or a solution of a compound with a pH greater than 7. For example and without limitation, the base is an alkaline hydroxide or an aqueous solution of an alkaline hydroxide. In certain embodiments, the base is NaOH or NaOH in PBS.

This "pre-gel" solution can, at that point be incubated at a suitably warm temperature, for example and without limitation, at about 37° C. to gel. The pre-gel can be frozen and stored at, for example and without limitation, −20° C. or −80° C. As used herein, the term "pre-gel solution" or "pre-gel" refers to a digest solution wherein the pH is increased. For example and without limitation, a pre-gel has a pH between 7.2 and 7.8.

Any type of extracellular matrix tissue can be used in the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666). In certain embodiments, the ECM is isolated from a vertebrate animal, for example and without limitation, from a warm blooded mammalian vertebrate animal including, but not limited to, human, monkey, pig, cow and sheep. The ECM can be derived from any organ or tissue, including without limitation, urinary bladder, intestine, liver, esophagus and dermis. In one embodiment, the ECM is isolated from a urinary bladder. The ECM may or may not include the basement membrane portion of the ECM. In certain embodiments, the ECM includes at least a portion of the basement membrane.

In another embodiment, the ECM is prepared by abrading porcine bladder tissue to remove the outer layers including both the tunica serosa and the tunica muscularis (layers G and F in FIG. 1) using a longitudinal wiping motion with a scalpel handle and moistened gauze. Following eversion of the tissue segment, the luminal portion of the tunica mucosa (layer H in FIG. 1) is delaminated from the underlying tissue using the same wiping motion. Care is taken to prevent perforation of the submucosa (layer E of FIG. 1). After these tissues are removed, the resulting ECM consists mainly of the tunica submucosa (layer E of FIG. 1).

The ECM can be sterilized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. More typically, ECM is disinfected by immersion in 0.1% (v/v) peracetic acid (G), 4% (v/v) ethanol, and 96% (v/v) sterile water for 2 h. The ECM material is then washed twice for 15 min with PBS (pH=7.4) and twice for 15 min with deionized water.

Commercially available ECM preparations can also be used in the methods, devices and compositions described herein. In one embodiment, the ECM is derived from small intestinal submucosa or SIS. Commercially available preparations include, but are not limited to, Surgisis™, Surgisis- ES™, Stratasis™, and Stratasis-ES™ (Cook Urological Inc.; Indianapolis, Ind.) and GraftPatch™ (Organogenesis Inc.; Canton Mass.). In another embodiment, the ECM is derived from dermis. Commercially available preparations include, but are not limited to Pelvicol™ (sold as Permacol™ in Europe; Bard, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

Tissue for preparation of ECM can be harvested in a large variety of ways and once harvested, a variety of portions of the harvested tissue may be used. For example and without limitation, in one embodiment, the ECM is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa (layers G, F, E and mostly D in FIG. 1) can be removed mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa (layer A of FIG. 1) can also be dissociated by soaking the tissue in a de-epithelializing solution, for example and without limitation, hypertonic saline. The resulting UBM comprises basement membrane of the tunica mucosa and the adjacent tunica propria (layers B and C of FIG. 1), which is further treated with peracetic acid, lyophilized and powdered. Additional examples are provided below and are also present in the related art.

In another embodiment, the epithelial cells can be delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

In one embodiment, the ECM is prepared by abrading porcine bladder tissue to remove the outer layers including both the tunica serosa and the tunica muscularis (layers G and F in FIG. 1) using a longitudinal wiping motion with a scalpel handle and moistened gauze. Following eversion of the tissue segment, the luminal portion of the tunica mucosa (layer H in FIG. 1) is delaminated from the underlying tissue using the same wiping motion. Care is taken to prevent perforation of the submucosa (layer E of FIG. 1). After these tissues are removed, the resulting ECM consists mainly of the tunica submucosa (layer E of FIG. 1).

The compositions described herein can be used in a number of ways or forms. For example and without limitation, according to a first embodiment, the pre-gel is placed in a suitable mold to model an organ or a portion thereof. As a non-limiting example, the composition is molded into a portion of a liver to facilitate re-growth of liver tissue. In another non-limiting example, the composition is molded in the shape of nose or ear cartilage, or a portion thereof, for replacement of damaged or excised cartilaginous tissue. In yet another non-limiting example, the composition is molded into the shape of a wound to facilitate non-scarring healing of that tissue. To prepare the molded gel, the pre-gel is placed in a biocompatible and preferably sterile mold, such as a plastic mold, and is incubated at a temperature and for a time suitable for gelation of the composition, for example and without limitation at about 37° C. In one embodiment, the composition and mold is placed in an incubator at 37° C. to gel. Because $CO_2$ has been found to slow gelation, in one non-limiting embodiment, $CO_2$ is not injected into the incubator, though in yet another embodiment, $CO_2$ and/or temperature may be used to control the gelation process.

Any useful cytokine, chemoattractant or cells can be mixed into the composition prior to gelation or diffused, absorbed and/or adsorbed by the gel after it is gelled. For example and without limitation, useful components include growth factors, interferons, interleukins, chemokines, monokines, hormones, angiogenic factors, drugs and antibiotics. Cells can be mixed into the neutralized solubilized gel or can be placed atop the molded composition once it is gelled. In either case, when the gel is seeded with cells, the cells can be grown and/or adapted to the niche created by the molded ECM gel by incubation in a suitable medium in a bioreactor or incubator for a suitable time period to optimally/favorably prepare the composition for implantation in a patient. The molded composition can be seeded with cells to facilitate in-growth, differentiation and/or adaptation of the cells. For example and without limitation, the cells can be autologous or allogeneic with respect to the patient to receive the composition/device comprising the gel. The cells can be stem cells or other progenitor cells, or differentiated cells. In one example, a layer of dermis obtained from the patient is seeded on a mold, for use in repairing damaged skin and/or underlying tissue.

As used herein, the terms "mold" refers to a cavity or surface used to form the gel into a three-dimensional shape. For example and without limitation, the mold can be a well plate, cell culture dish or a tube or can be shaped into any useful shape. In a certain embodiment, the mold can be shaped into a certain organ or part of an organ. The gel can be delivered to the mold in a variety of methods, including, but not limited to, injection, deposition.

As used herein, the terms "drug" and "drugs" refer to any compositions having a preventative or therapeutic effect, including and without limitation, antibiotics, peptides, hormones, organic molecules, vitamins, supplements, factors, proteins and chemoattractants.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

One favorable aspect of the use of pre-molded tissue is that a layered composition can be produced. For example, a core portion of the composition to be implanted can be prepared with a first ECM gel, obtained from a first source, and a surrounding layer can be with a second ECM gel, obtained from a second source different from the first, or the same source as the first, but containing different constituents, such as cytokines or cells.

In another embodiment of the pre-molded composition, the ECM gel is contained within a laminar sheath of non-comminuted and non-digested ECM tissue, such as SIS or UBM, to add physical strength to the gel. In this embodiment, sheets of ECM tissue, prepared in any manner known in the art, can be placed into the mold prior to filling the mold with the solubilized ECM tissue for producing the gel. The sheets of ECM tissue may be used as the mold, so long as they are formed and sewn or cross-linked into a desired shape. In this manner, a solid composition can be produced that has greater physical strength than is the case of a gel, alone.

In another non-limiting embodiment, the composition is injected as a pre-gel into a patient. The composition is injected at a locus in the patient where the matrix is needed for cell growth. For example and without limitation, where a patient has had tissue removed due to trauma, debridement and/or removal of damaged, diseased or cancerous tissue, the composition can be injected at the site of tissue removal to facilitate in-growth of tissue. The viscosity of the pre-gel can be controlled by varying the amounts of water (e.g., by varying the amounts of water, acid, base, buffer (such as PBS) or other diluents) used to prepare the pre-gel. In applications in which a small gauge needle is used, such as in endoscopy, a less viscous pre-gel would be needed, which typically results in a less viscous gel, once the pre-gel is gelled. In applications in which a larger gauge needle is available, a more viscous gel, with higher strength when gelled, can be used. Also, use of a larger gauge needle, irrespective of the viscosity of the pre-gel, favors mixing of live cells with the pre-gel immediately prior to implantation with less risk of shearing the cells.

In one embodiment, a pre-gel is prepared by raising the pH of the acidic digest solution and the pre-gel is directly injected into a patient prior to significant gelation proceeds. In one embodiment, the pre-gel is in a frozen state and is thawed and warmed prior to injection. In another embodiment, the acidic digest solution is warmed to physiological temperature and is mixed during injection in a static mixer with suitable quantities of a base and/or buffer, such as PBS. Suitable static mixers include, without limitation, helical or square static mixers, commercially available from Cammda Corporation of Cobourg, Ontario, Canada or a Mini-Dual Syringe with Micro Static Mixer commercially available from Plas-Pak Industries, Inc. of Norwich, Conn.

In a further embodiment, a commercial kit is provided comprising a composition described herein. A kit comprises suitable packaging material and the composition. In one non-limiting embodiment, the kit comprises a pre-gel in a vessel, which may be the packaging, or which may be contained within packaging. In this embodiment, the pre-gel typically is frozen or kept at near-freezing temperatures, such as, without limitation, below about 4° C. In another non-limiting embodiment, the kit comprises a first vessel containing an acidic solution comprising digest solution of ECM as described herein, and a second vessel comprising a neutralizing solution comprising a base and/or buffer(s) to bring the acidic solution of the first vessel to physiological ionic strength and pH, to form a pre-gel. This kit also optionally comprises a mixing needle and/or a cold-pack. The vessel may be a vial, syringe, tube or any other container suitable for storage and transfer in commercial distribution routes of the kit.

In yet another embodiment of the kit, a pre-gel composition is molded and pre-gelled prior to packaging and distribution. In one embodiment, the molded gel is packaged in a blister-pack comprising a plastic container and a paper, plastic and/or foil sealing portion, as are well-known in the art. The mold and packaging typically is sterilized prior to or after packaging, for example and without limitation, by gamma irradiation. The molded composition may be packaged in any suitable physiological solution, such as PBS or saline. If the molded gel contains live cells, the mold can be transported in a suitable cell-culture medium in a sealed jar or other vessel. Of course, the cell-containing molded gel would have to be shipped in an expedited manner to preserve the cells.

As used herein, the term "hybrid inorganic/ECM scaffold" refers to a ECM-derived gel that is coated onto a biocompatible inorganic structure, such as, without limitation, a metal, an inorganic calcium compound such as calcium hydroxide, calcium phosphate or calcium carbonate, or a ceramic composition. In one embodiment, ultrasonication is used to aid in coating of the inorganic structure with the ECM-derived gel. As used herein, the term "ultrasonication" refers to the process of exposing ultrasonic waves with a frequency higher than 15 kHz and lower than 400 kHz.

As used herein, the term "coat", and related cognates such as "coated" and "coating," refers to a process comprising of covering an inorganic structure with ECM-derived gel or hybrid inorganic/ECM scaffold. For example and without limitation, coating of an inorganic structure with ECM-derived gel can include methods such as pouring, embedding, layering, dipping, spraying.

In another embodiment of the technology described herein, the composition is coated onto a biocompatible structural material, such as a metal, an inorganic calcium compound such as calcium hydroxide, calcium phosphate or calcium carbonate, or a ceramic composition. Non-limiting examples of suitable metals are cobalt-chrome alloys, stainless steel alloys, titanium alloys, tantalum alloys, titanium-tantalum alloys, which can include both non-metallic and metallic components, such as molybdenum, tantalum, niobium, zirconium, iron, manganese, chromium, cobalt, nickel aluminum and lanthanum, including without limitation, CP Ti (commercially pure titanium) of various grades or Ti 6Al 4V (90% wt. Ti, 6% wt. Al and 4% wt. V), stainless steel 316, Nitinol (Nickel-titanium alloy), titanium alloys coated with hydroxyapatite. Metals are useful due to high strength, flexibility, and biocompatibility. Metals also can be formed into complex shapes and many can withstand corrosion in the biological environments, reduce wear, and not cause damage to tissues. In one non-limiting example, the metal is femoral or acetabular component used for hip repair. In another example, the metal is a fiber or other protuberance used in permanent attachment of a prosthesis to a patient. Other compositions, including ceramics, calcium compounds, such as, without limitation, aragonite, may be preferred, for example and without limitation, in repair of or re-shaping of skeletal or dental structures. Combinations of metal, ceramics and/or other materials also may prove useful. For instance, a metal femoral component of a hip replacement may comprise a ceramic ball and/or may comprise a plastic coating on the ball surface, as might an acetabular component.

Metals, as well as other materials, as is appropriate, can be useful in its different forms, including but not limited to wires, foils, beads, rods and powders, including nanocrystalline powder. The composition and surface of metals or other materials can also be altered to ensure biocompatibility, such as surface passivation through silane treatments, coating with biocompatible plastics or ceramics, composite metal/ceramic materials. The materials and methods for their employment are well-known in the field of the present invention.

A difficulty with using metal inserts to repair a patient's skeletal structure is that the inserts must be anchored/attached to existing skeletal parts. Traditional methods employed cement and/or screws. In the case of prostheses, the prostheses are not connected to a patient's tissue except, typically, by cementing. Therefore, it is desirable to biologically attach a patient's tissue to a medical device. This may be accomplished by coating surfaces of the implant with the ECM gel described herein, which will facilitate in-growth of tissue and thus attachment of the device. A variety of porous structures can be attached to the implant to create a scaffold into which the ECM gel, and later cells or other tissue (e.g., bone) can infiltrate. Structures include, without limitation: woven or non-woven mesh, sponge-like porous materials, fused beads, etc. The porous scaffold will facilitate formation of a strong bond between living tissue, including bone, and the device. The "pores" of the porous scaffold may be of any size that will permit infiltration of an ECM gel, optionally facilitated by ultrasound or other treatments that would assist in permeation of the gel, and later cells or other biological materials, such as bone, cartilage, tendons, ligaments, fascia or other connective tissue, into the scaffolding. In one embodiment, metal fibers are attached to the device, and the metal fibers are coated with an ECM gel described herein, thereby permitting in-growth of tissue within the fibers. In a second embodiment, a matrix of small beads is welded or otherwise attached to a surface of the device and an ECM gel described herein is coated onto the bead matrix, facilitating in-growth of tissue among the beads. In one example, a device contains a protuberance of fibers, which can be inserted inside a bone, permitting fusion of the metal fibers with the bone. In one embodiment, the ECM gel is seeded and incubated with a suitable cell population, such as autologous osteoblasts, to facilitate bone in-growth.

Figure 19:
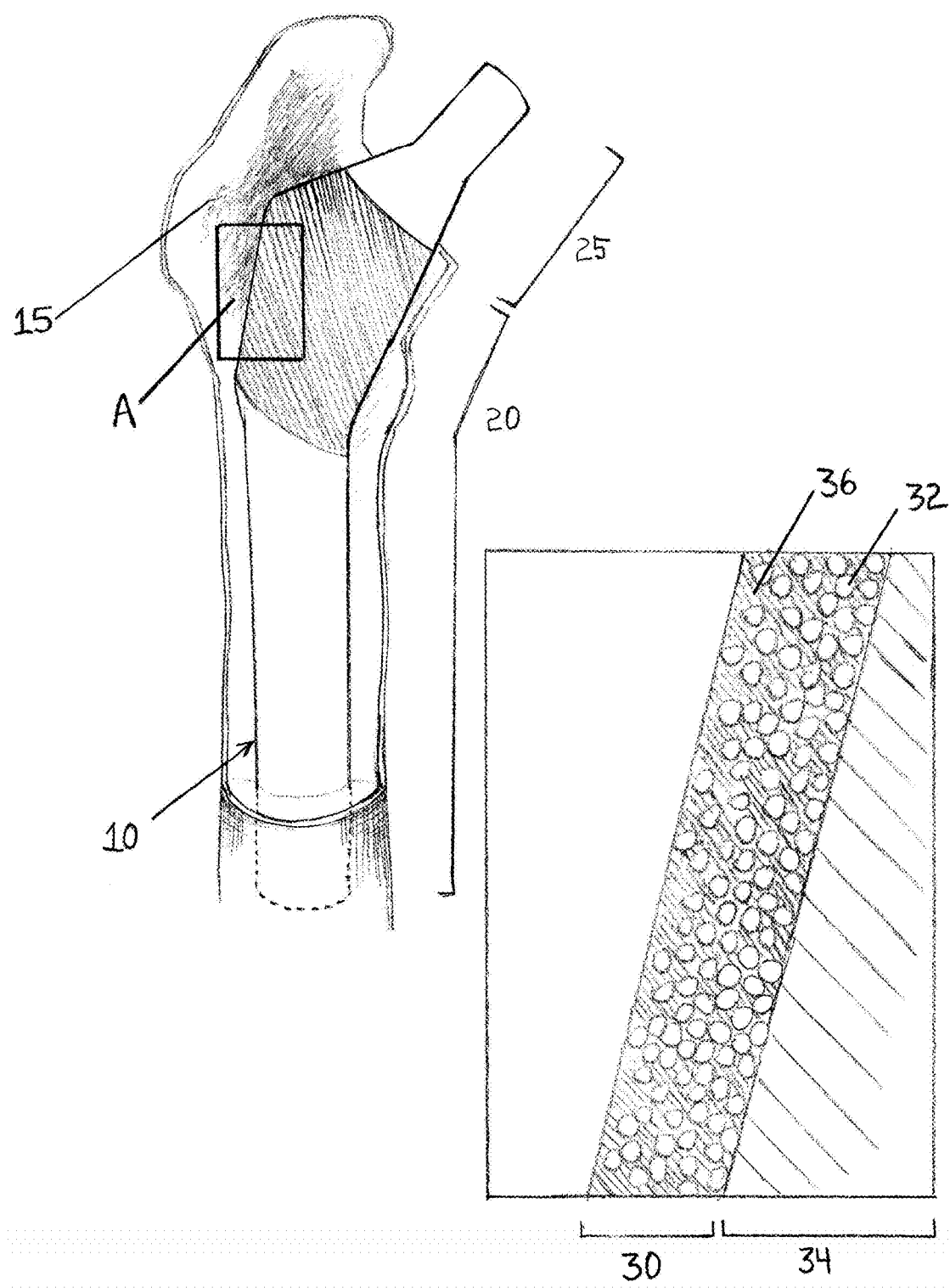
FIG. 19 shows schematically one embodiment of a femoral implant described herein.

In another embodiment, the hybrid inorganic/ECM scaffold can also be used to coat other structural implants, such as, without limitation, a femoral implant, a prosthesis of the hand. FIG. 19 shows schematically one embodiment of a device 10 inserted into a femur 15 in a hip replacement procedure. FIG. 19 illustrates device 10, showing an insert portion 20 for insertion into femur 15, and an extension 25 into which a ball (not shown) is screwed or otherwise inserted. Device 10 comprises a porous coating 30 of, for example and without limitation, metal beads welded onto the device 10. Region A in FIG. 19 shows a magnified view of coating 30 of device 10. Beads 32 are welded to metal surface 34 of device 10. ECM gel 36 is coated onto and between beads 32. Bone tissue growth into beads 32 is facilitated by the presence of the ECM gel 36.

Figure 20:
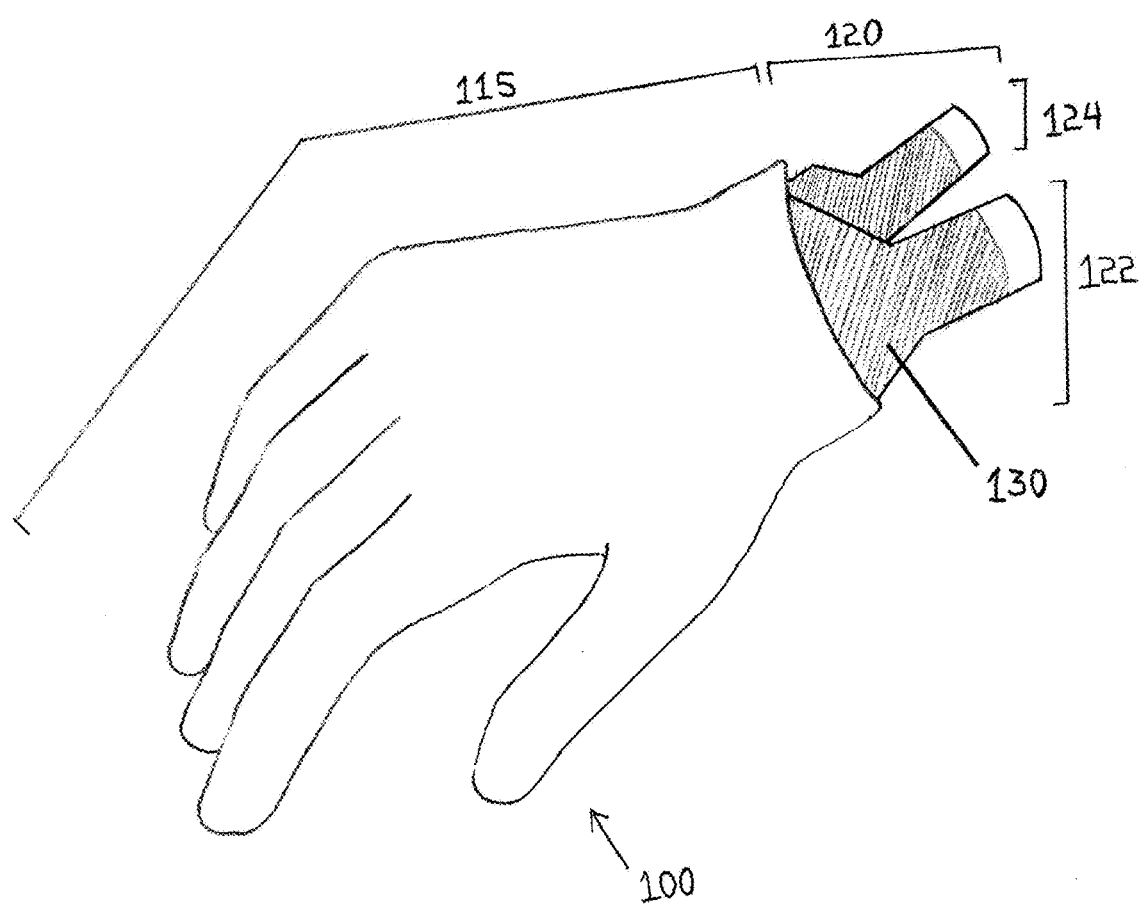
FIG. 20 shows schematically one embodiment of a hand prosthesis described herein.

A prosthesis might be anchored into bone in a like manner using an insert having a porous coating, with the porous coating extending to the limits of where attachment to a patient's tissue is desired. As an example, shown in FIG. 20, a hand prosthesis 100 comprises an external portion 115 and an internal portion 120, which comprises a radius insert portion 122 and an ulnar insert portion 124. Porous coating 130 extends from insert portions 122 and 124 for attachment to bone, to the beginning of external portion 115, permitting attachment of dermis and intermediary tissue between the bones and dermis.

In use, the device which is coated with a suitable scaffolding and ECM gel as described herein may be contacted with cells, e.g. of a patient or allogeneic cells, and the cells are allowed to infiltrate the matrix. The in-growth or infiltration of cells can occur in vivo or ex vivo, depending on optimization of methods. For example and without limitation, in the case of a femoral implant, the implant can be inserted into the femur and cells of a patient, and desirable bone tissue, infiltrates the scaffolding to fuse the device to the bone. In another embodiment, for example in the case of an artificial tendon or ligament, a biopsy of a patient's tendons or ligaments is incubated with an appropriate scaffold in order to create an autologous ligament or tendon graft.

EXAMPLES

Example 1—Preparation of Porcine Extracellular Matrix (ECM) (UBM)

The preparation of UBM has been previously described [Sarikaya A, et al. Tissue Eng. 2002 February; 8(1):63-71; Ringel R L, et al. J Speech Lang Hear Res. 2006 February; 49(1):194-208]. In brief, porcine urinary bladders were harvested from 6-month-old 108-118 kg pigs (Whiteshire-Hamroc, Ind.) immediately following euthanasia. Connective tissue and adipose tissue were removed from the serosal surface and any residual urine was removed by repeated washes with tap water. The tunica serosa, tunica muscularis externa, the tunica submucosa, and majority of the tunica muscularis mucosa were mechanically removed. The urothelial cells of the tunica mucosa were dissociated from the luminal surface by soaking the tissue in 1.0 N saline solution yielding a biomaterial composed of the basement membrane plus the subjacent tunica propria, which is referred to as urinary bladder matrix (UBM).

The UBM sheets were disinfected for two hours on a shaker in a solution containing 0.1% (v/v) peracetic acid, 4% (v/v) ethanol, and 95.9% (v/v) sterile water. The peracetic acid residue was removed by washing with sterile phosphate-buffered saline (pH=7.4) twice for 15 minutes each and twice for 15 minutes each with sterile water. The UBM sheets (as in FIG. 2A) were then lyophilized (FIG. 2B) using a FTS Systems Bulk Freeze Dryer Model 8-54 and powdered using a Wiley Mini Mill.

One gram of lyophilized UBM powder (FIG. 2B) and 100 mg of pepsin were both mixed in 100 ml of 0.01 M HCl. The solution was kept at a constant stir for ~48 hrs at room temperature (25° C.). After pepsin digestion, the digest solution (FIG. 1C) was aliquoted and stored at −20° C. until use. After completion, the solution is referred to as digest solution or ECM digest or ECM stock solution.

Example 2—Preparation of Porcine Spleen ECM

Fresh spleen tissue was obtained. Outer layers of the spleen membrane were removed by slicing, where remaining tissue was cut into uniform pieces. Remnants of outer membrane were trimmed, then rinsed three times in water. Water was strained by using a sieve. Splenocytes were lysed by massaging. Spleen slices were incubated in a solution of 0.02% trypsin/0.05% EDTA at 37° C. for 1 hour in a water bath. If necessary, splenocytes were further lysed by massaging. After rinsing, slices were soaked in 3% Triton X-100 solution and put on a shaker for 1 hour. If necessary, splenocytes were further lysed by massaging. Slices were then soaked in 4% deoxycholic acid solution and put on a shaker for 1 hour. After thoroughly rinsing, the purified spleen ECM was stored for further processing. This tissue was next disinfected with peracetic acid treatment and dried.

One gram of dry porcine spleen ECM and 100 mg of pepsin were both mixed in 100 ml of 0.01 M HCl. The solution was kept at a constant stir for ~72 hrs at room temperature (25° C.). If there are no visible pieces of the ECM floating in the solution, aliquot the sample and freeze (−20° C.) or use immediately.

Example 3—Preparation of Porcine Liver Stroma ECM

Fresh liver tissue was obtained. Excess fat and tissue were trimmed. Outer layers of the liver membrane were removed by slicing, where remaining tissue was cut into uniform pieces. Remnants of outer membrane were trimmed using a scalpel or razor blade, then rinsed three times in water. Water was strained by using a sieve. Cells were lysed by massaging. Liver slices were incubated in a solution of 0.02% trypsin/0.05% EDTA at 37° C. for 1 hour in a water bath. If necessary, cells were further lysed by massaging. After rinsing, slices were soaked in 3% Triton X-100 solution and put on a shaker for 1 hour. If necessary, cells were further lysed by massaging. Slices were then soaked in 4% deoxycholic acid solution and put on a shaker for 1 hour. After thoroughly rinsing, the purified liver stroma was stored in deionized water for further processing. This tissue was next disinfected with peracetic acid treatment and dried.

One gram of dry porcine liver stroma ECM and 100 mg of pepsin were both mixed in 100 ml of 0.01 M HCl. The solution was kept at a constant stir for ~24-48 hrs at room temperature (25° C.). If there are no visible pieces of the ECM floating in the solution, aliquot the sample and freeze (−20° C.) or use immediately.

Example 4—Preparation of Human Liver Stroma ECM

Fresh liver tissue was obtained. Excess fat and tissue were trimmed. Outer layers of the liver membrane were removed by slicing, where remaining tissue was cut into uniform pieces. Remnants of outer membrane were trimmed using a scalpel or razor blade, then rinsed three times in water. Water was strained by using a sieve. Cells were lysed by massaging. Liver slices were incubated in a solution of 0.02% trypsin/0.05% EDTA at 37° C. for 1 hour in a water bath. If necessary, cells were further lysed by massaging. After rinsing, slices were soaked in 3% Triton X-100 solution and put on a shaker for 1 hour. If necessary, cells were further lysed by massaging. Slices were then soaked in 4% deoxycholic acid solution and put on a shaker for 1 hour. After thoroughly rinsing, the purified liver stroma was stored in deionized water for further processing. This tissue was next disinfected with peracetic acid treatment and dried.

One gram of dry human liver stroma ECM and 200 mg of pepsin were both mixed in 50 ml of 0.01 M HCl. The solution was kept at a constant stir for ~3-5 days at room temperature (25° C.). The solution will need to be monitored every day. If there are no visible pieces of the ECM floating in the solution, aliquot the sample and freeze (−20° C.) or use immediately.

Example 5—Preparation of Porcine Cardiac ECM

One gram of dry porcine cardiac ECM with 100 mg of pepsin were both mixed in 50 mL of 0.01 M HCl. The solution was kept at a constant stir for ~48 hours at room temperature (25° C.).

Example 6—Preparation of Porcine Pancreatic ECM

One gram of dry de-fatted porcine pancreatic ECM with 100 mg of pepsin were both mixed in 50 mL of 0.01 M HCl. The solution was kept at a constant stir for ~48 hours at room temperature (25° C.).

Example 7—Preparation of Porcine Ovarian ECM

Fresh ovarian tissue is obtained within 6 hours of harvest. Ovaries were removed and stored in physiological saline tissue until ready for dissection and residual uterine tissue was removed. Longitudinal incisions were made through the hilum of the ovary and the follicles were disrupted. Once all the follicles have been disrupted, the ECM has been harvested from the ovaries. Rinse three times in filtered water and strain the water using a sieve. Cells were lysed by gentle massaging. ECM was incubated in a solution of 0.02% trypsin/0.05% EDTA at 37° C. for 1 hour in a water bath and then rinsed. If necessary, cells were further lysed by massaging. ECM was soaked in 3% Triton X-100 solution and put on a shaker for 1 hour. After rinsing, cells were further lysed by massaging if necessary. Slices were then soaked in 4% deoxycholic acid solution and put on a shaker for 1 hour. After thoroughly rinsing to remove residual surfactant, the ECM was stored in sterile/filtered water until further use. This tissue was next disinfected with peracetic acid treatment and dried.

One gram of lyophilized ovarian ECM powder and 100 mg of pepsin were both mixed in 100 ml of 0.01 M HCl. The solution was kept at a constant stir for ~48 hrs at room temperature (25° C.). After pepsin digestion, the digest solution was aliquoted and stored at −20° C. until use.

Example 8—General Method of Preparation of Gels from ECM

UBM gel was formed into a gel by mixing 0.1 N NaOH (1/10 of the volume of digest solution) and 10×PBS pH 7.4 (1/9 of the volume of digest solution) in appropriate amounts at 4° C. The solution was brought to the desired volume and concentration using cold (4° C.) 1×PBS pH 7.4 and placed in a 37° C. incubator for gelation to occur (FIG. 2D).

Figure 2:
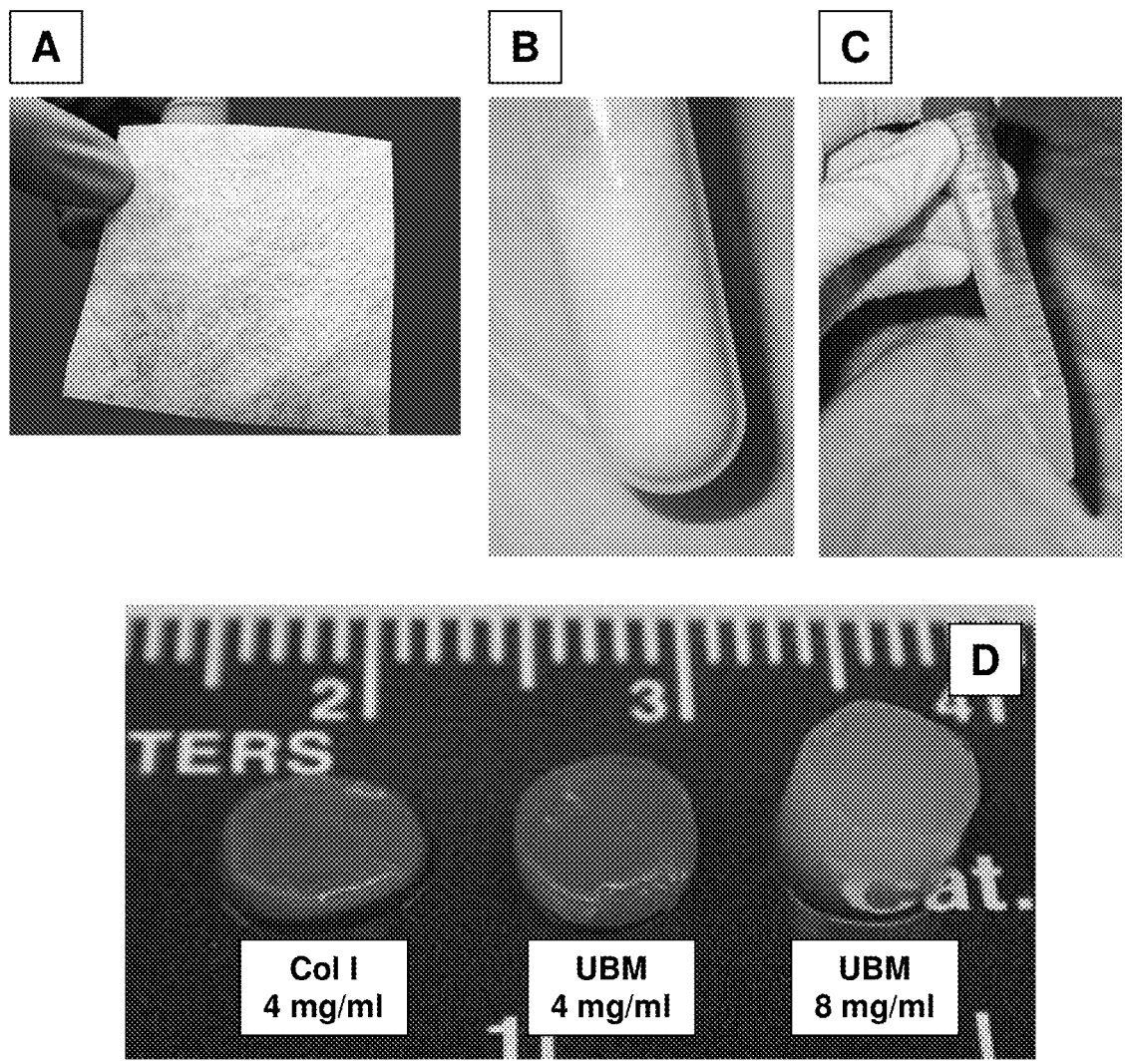
FIG. 2 shows photographs of the porcine urinary bladder matrix (UBM) in its different forms: lyophilized UBM sheet (A), lyophilized UBM powder (B); pepsin-digested solution at a concentration of 10 mg/ml of UBM (C), and gels at 4 mg/ml of UBM and at 8 mg/ml of UBM, where a gel of collagen I (Col I) at 4 mg/ml is shown for comparison (D).

The ECM was able to form a matrix after 40 minutes in solution as shown in FIG. 2. The ECM-derived gel was liquid at temperatures below 20° C. but turn into a gel when the temperature is raised to 37° C.

In preparing gels from ECM, all of the following solutions should be kept on ice and the following variables must be determined:

$C_f$=concentration of the final gel in mg/ml
$C_s$=concentration of the ECM digest solution in mg/ml
$V_f$=volume of the final gel solution needed for the experiments
$V_d$=volume needed from the ECM digest solution in ml
$V_{10X}$=volume of 10×PBS needed in ml
$V_{1X}$=volume of 1×PBS needed in ml
$V_{NaOH}$=volume of 0.1 N NaOH needed in ml First, determine the final concentration (Cf) and volume (Vf) of ECM gel required. Then, calculate the mass of ECM needed by multiplying Cf (mg/ml)*Vf (ml). This value will give you the volume needed from the ECM digest solution (Vd), where Vd=[Cf (mg/ml)*Vf (ml)]/Cs.

Calculate the volume of 10×PBS needed by dividing the calculated volume Vd by 9 (V10×=Vd/9). Calculate the volume of 0.1 N NaOH needed by dividing the calculated volume Vd by 10 (VNaOH=Vd/10). Calculate the amount of 1×PBS needed to bring the solution to the appropriate concentration/volume as follow: V1×=Vf−Vd−V10×−VNaOH. Add all the reagents (V1×+Vd+V10×+VNaOH) to an appropriate container (usually 15 or 50 ml centrifuge tubes) without the ECM digest (Vd). Place solutions on ice and keep on ice at all times.

Add the appropriate volume from the ECM digest solution (Vd) to the PBS/NaOH mixture prepared above and mix well with a 1ml micropipette while being careful and avoiding the creation of air bubbles in the solution. Depending on the viscosity of the ECM digest solution, there might be some significant volume loss during the transfer. Monitor the total volume and add appropriate amounts until the final volume is achieved. Measure the pH of the pre-gel solution, where pH should be around 7.4.

Add the pre-gel solution to a mold or to appropriate wells. Place the mold or wells in 37° C. incubator for a minimum of 40 minutes. Avoid using an incubator with CO2 control. If water evaporation is a concern, place the mold inside a plastic zip-lock bag before placing in the incubator. After gelation, the gel can be removed from the mold and placed on 1×PBS. If the gels were made in tissue culture plates, 1×PBS can be placed on top of the gels until use to maintain the gels hydrated.

Sample calculation: Make 6 ml of gel with a final concentration of 6 mg/ml from the 10 mg/ml stock solution.
GIVEN: $C_s$=10 mg/ml; $C_f$=6 mg/ml; $V_f$=6 ml
$V_d$=[6 mg/ml*6 ml]/10 mg/ml=3.600 ml
$V_{10×}$=3.6/9=0.400 ml
$V_{NaOH}$=3.6/10=0.360 ml
$V_{1×}$=6 ml−3.6 ml−0.400 ml−0.360=1.640 ml Example 9—Composition and Morphology of Porcine UBM UBM and rat-tail collagen type I (BD, Biosciences) solutions were electrophoresed on 4-20% polyacrylamide gels under reducing conditions (5% 2-Mercaptoethanol). The proteins were visualized with Gel-Code Blue (Bio-Rad), and documented by a Kodak imaging station.

Collagen and sulfated glycosaminoglycan (S-GAG) content were determined using the hydroxyproline assay [Reddy G K, Enwemeka C S. A simplified method for the analysis of hydroxyproline in biological tissues. Clin Biochem. 1996 June; 29(3):225-9] and the Blyscan™ assay kit (Biocolor, Northern Ireland) respectively (three samples were tested). The Blyscan™ assay was performed according to the manufacturer's instruction. The hydroxyproline content was determined by hydrolyzing the samples with 2 M NaOH (100 μl total volume) in an autoclave at 120° C. for 20 minutes. The samples were neutralized with 50 al of 4 M HCl and reacted with 300 al of 0.056 M chloramine-T (Spectrum), mixed gently, and allowed to oxidize for 25 minutes at room temperature. The samples were then mixed with 300 al of 1 M Ehrlich's aldehyde (Spectrum) and incubated at 65° C. for 20 minutes. A standard curve was generated using rat-tail collagen type I (BD Biosciences) and used to calculate the total amount of collagen present in the digested UBM solutions. The colorimetric change was determined by the absorbance at 550 nm using a SpectraMax spectrophotometer.

Figure 3:
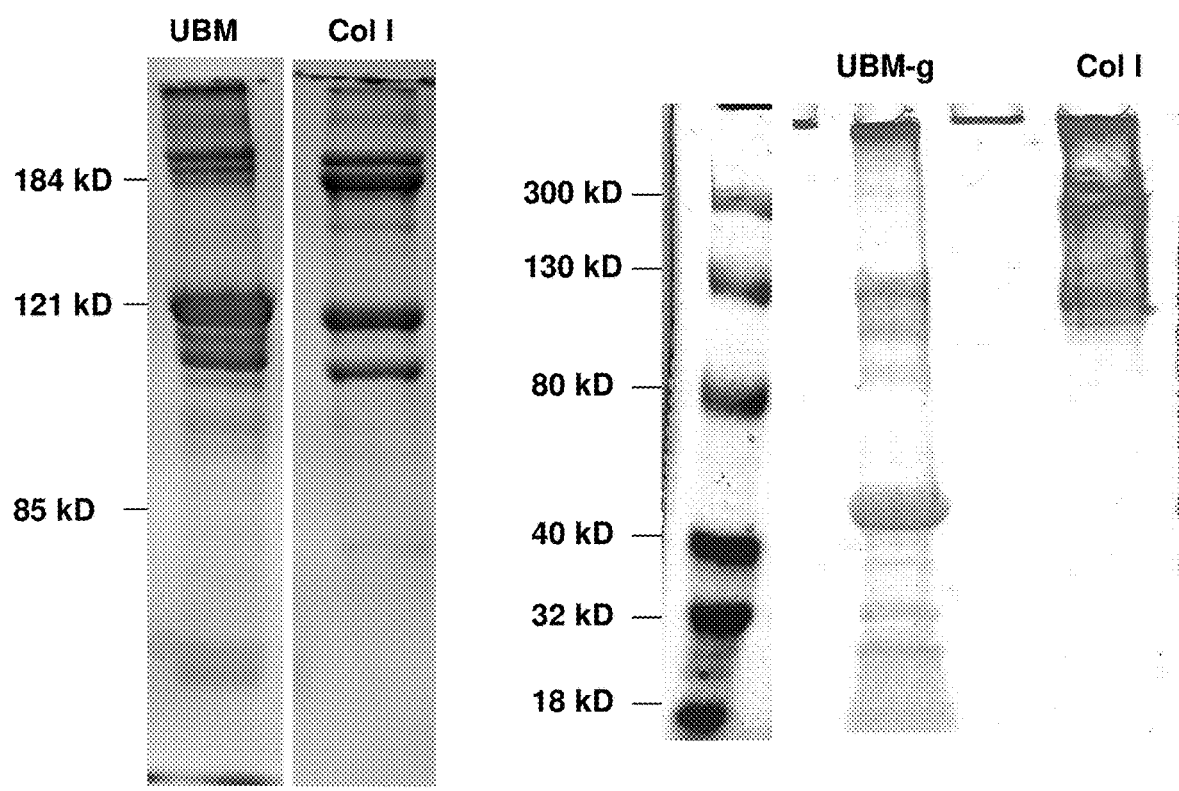
FIG. 3 shows results from gel-electrophoresis of UBM and Col I gels.
Figure 4:
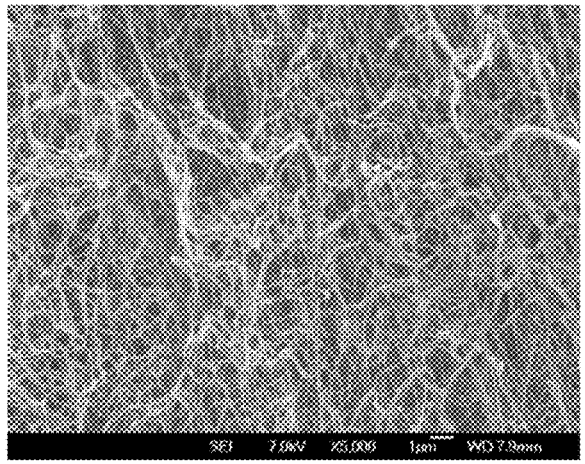
FIG. 4 shows scanning electron micrograph (SEM) images of UBM gels at different concentrations and at different magnifications: 3 mg/ml UBM gel at 5,000× (A) and at 10,000× (B); and 6 mg/ml UBM gel at 5,000× (C) and at 10,000× (D).
Figure 4:
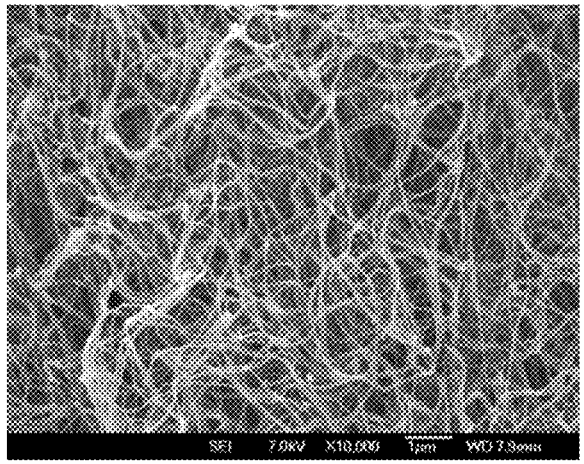
Figure 4:
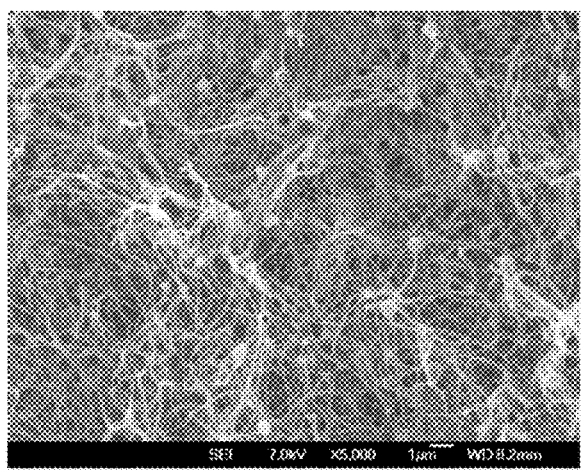
Figure 4:
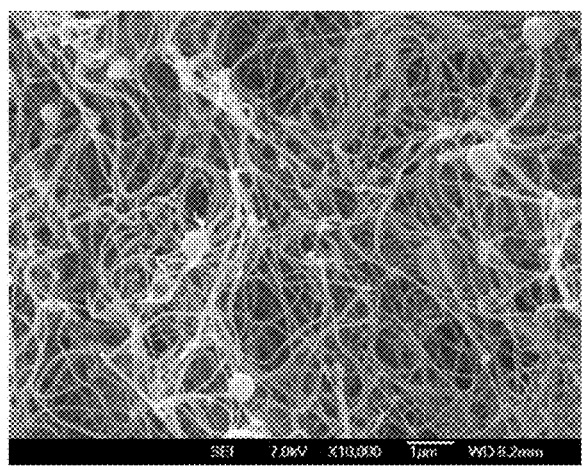

The composition of the gel has been determined. The collagen concentration for pepsin digested UBM was found to be 0.8±0.2 mg per mg of dry lyophilized UBM powder (mean±SD). The total S-GAG content was found to be 5.1±0.9 ag per mg of dry lyophilized UBM powder (mean±SD). The electrophoresed proteins show the typical bands for collagen type I present on the UBM lane with extra bands as shown in FIG. 3. The difference may be in part due to the additional components, that is, to small peptides and glycosaminoglycans) present in the UBM gels.

Figure 5:
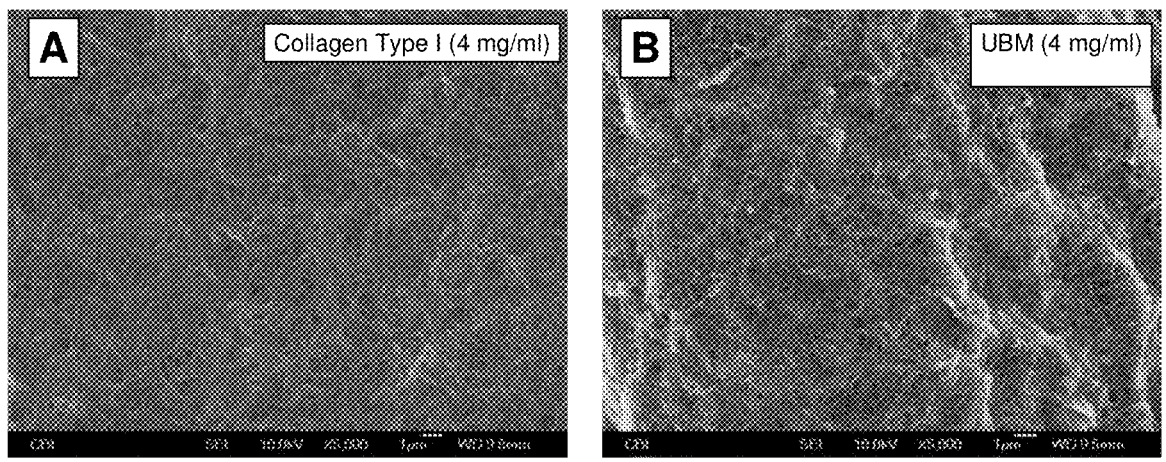
FIG. 5 shows SEM images of a 4 mg/ml Col I gel and of a 4 mg/ml UBM gels at a magnification of 5,000×.

The surface morphology of the UBM gels was examined using a scanning electron microscope (SEM). The specimens were fixed in cold 2.5% glutaraldehyde and rinsed in PBS, followed by a dehydration process through a graded series of ethanol (30% to 100%), and finally critically point dried in an Emscope CPD 750 critical point dryer. The samples were attached to aluminum SEM specimen mounting stubs (Electron Microscopy Sciences, Hatfield, Pa.) and sputter coated with a gold palladium alloy using a Sputter Coater 108 Auto (Cressington Scientific Instruments, Valencia, Pa.). Finally, samples were examined using a scanning electron microscope (JEOL 6330F). Images were taken at a 5,000 and 10,000× magnification. The scanning electron microscopy pictures show the fibrillar appearance of the UBM gels at concentrations of 3 mg/ml and 6 mg/ml (FIG. 4A-4D) as well as at 4 mg/ml (FIG. 5B).

Example 10—Rheological Properties and Gelation Kinetics of Porcine UBM, SIS and LS Gels The rheological properties of the UBM derived gel was characterized during gelation. The UBM gel consists of a viscous solution at temperature below 25° C. and a gel at physiological temperatures (37° C.). Rheological properties of other gels can be measured using similar methods described herein. Rheological properties of liver stroma (LS) and small intestine submucosa (SIS) were also measured.

Turbidimetric gelation kinetics was determined spectrophotometrically as previously described [Gelman R A, et al. Collagen fibril formation. Evidence for a multistep process. J Biol Chem. 1979 Jan. 10; 254(1):180-6]. Final pre-gel solutions at the appropriate concentration were kept at 4° C. and transferred to a cold 96 well plate by placing 100 al per well in triplicates. The SpectraMax spectrophotometer (Molecular Devices) was pre-heated to 37° C., the plate was placed in the spectrophotometer, and the turbidity of each well was measured at 405 nm every 2 minutes for 1.5 hours (FIG. 6A). Turbidity can also be measured at 530 nm (FIG. 7). The absorbance values were recorded and normalized as shown in FIG. 6B. The time needed to reach 50% of the maximum turbidity measurement (e.g. maximum absorbance value) was defined as t1/2 and the lag phase (tlag) was calculated by extrapolating the linear growth of the curve. The speed (S) of the gelation based on turbidimetric measurements was determined by calculating the slope of the growth portion of the curve as shown in FIG. 6B.

Dynamic oscillatory measurements are commonly used in fundamental studies of gelation and in characterizing the viscoelastic properties of gels. The sample was subjected to an oscillatory strain of:

$$\gamma(t)=\gamma_0 \cos(2\pi f t) \quad (1)$$

where $\gamma_0$ was the amplitude of the sinusoidal strain, t was the time, and f was the frequency. The sample developed a sinusoidal stress described as follow:

$$\sigma(t)=|G^*|\gamma(t) \quad (2)$$

where G* was the frequency dependent complex modulus of the sample. The real part of G*, denoted G', was in phase with the applied strain and was called the storage modulus since it corresponded to storage of mechanical energy in the elastic deformation of the sample. The imaginary portion of G*, denoted G", was 90° out of phase with the applied strain and was called the loss modulus since it corresponded to the loss of energy by viscous dissipation within the sample. Since the sample was expected to develop solid-like characteristics as gelation proceeds, G' was expected to increase significantly.

A final property of interest was the magnitude of the complex viscosity defined as follows:

$$|\eta^*| = \frac{|G^*|}{2\pi f} = \frac{\sqrt{G'^2 + G''^2}}{2\pi f} \quad (3)$$

where $|\eta^*|$ was the frequency dependent complex viscosity, G* was the frequency dependent complex modulus, and f was the frequency. It is common to fit complex viscosity versus frequency data to a power-law of the form:

$$|\eta^*| = kf^n \quad (4)$$

where k and n are both constants.

Rheological experiments were performed with a TA Instruments AR2000 stress-controlled rheometer using a 40 mm-diameter parallel plate geometry and a Peltier cell to maintain the sample temperature. The samples were prepared as discussed earlier and loaded into the rheometer with the Peltier cell maintaining a temperature of 15° C. The sample edge was protected from evaporation by applying mineral oil. The viscosity of the sample was first measured by applying a constant stress of 1 Pa on the sample for one minute at 15° C. The temperature was then set to 37° C. to induce gelation; the Peltier cell typically reached a temperature of 30° C. within 10 seconds and 37° C. within 50 seconds. During this increase in temperature and the subsequent gelation, the oscillatory moduli of the sample were monitored continuously at a fixed frequency of 0.159 Hz (1 rad/s) and a strain of 5%. When there was no further change in the elastic modulus (G') with time, gelation was deemed to be complete. The final linear viscoelastic properties of the gel were measured by performing a frequency sweep between 15.9 Hz and 0.08 Hz at 37° C. and 5% strain and fitted to equation 4.

Figure 6:
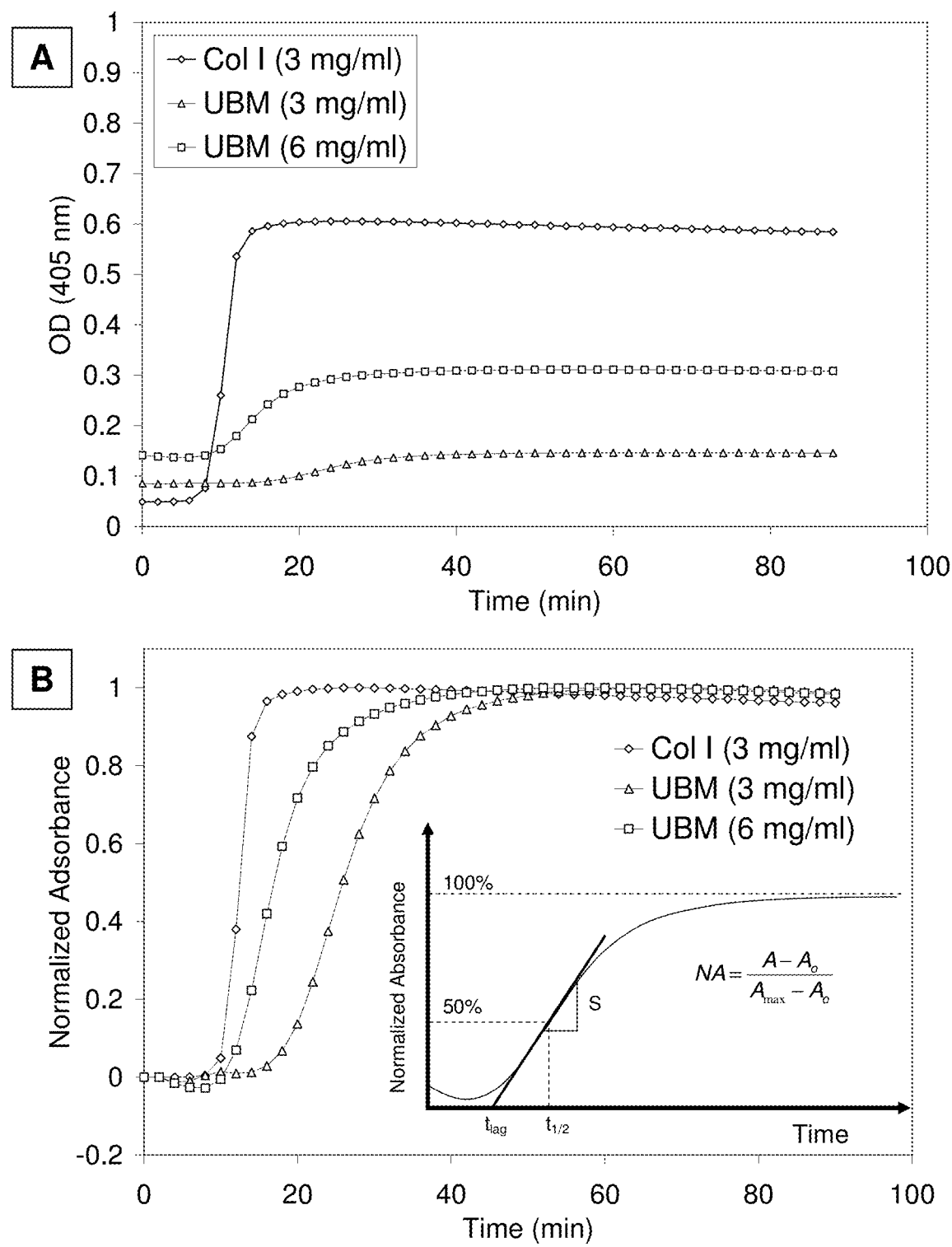
FIG. 6 shows turbidimetric gelation kinetics of Col I gels and UBM gels, which was determined spectrophotometrically by measuring absorbance during gelation. Results are shown for both measured absorbance values (A) and normalized absorbance values (B), which allows for calculating kinetic parameters such as t1/2 (time to reach 50% of maximum turbidity), tlag (lag time of gelation) and S (speed of gelation).
Figure 7:
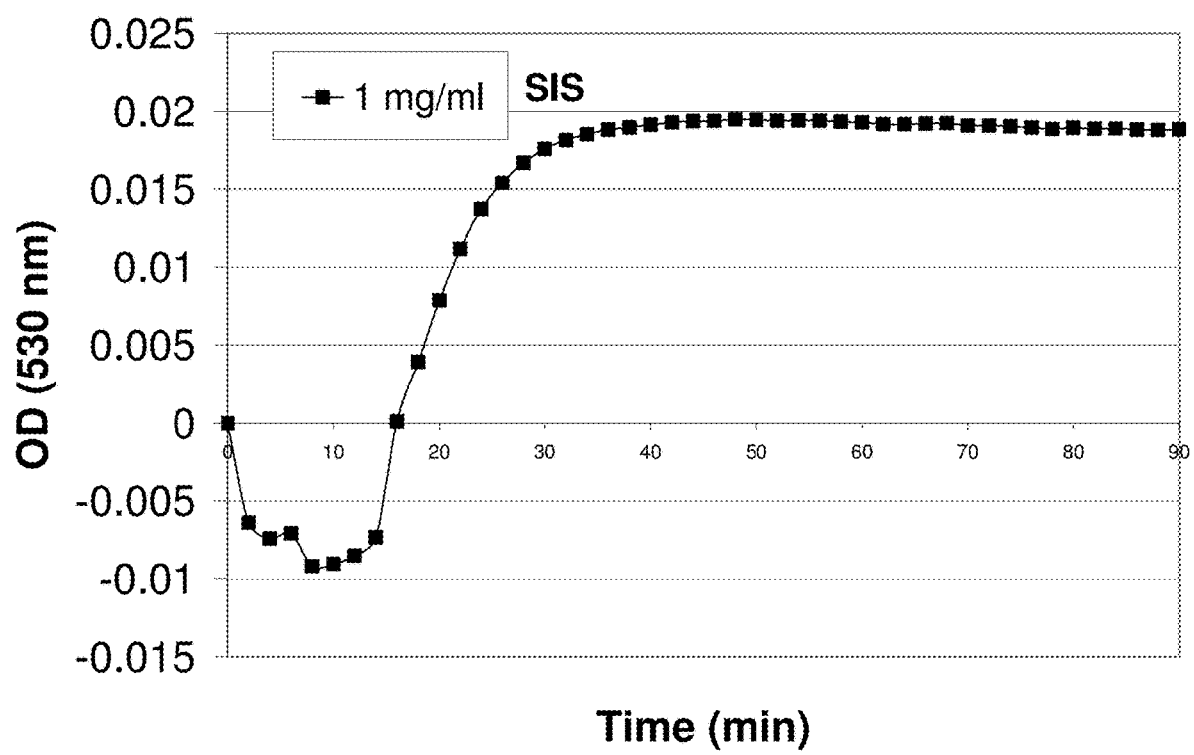
FIG. 7 shows turbidimetric gelation kinetics of 1 mg/mL small intestine submucosa (SIS) gels.

The turbidimetric gelation kinetics and the calculated parameters are shown in FIG. 6 and the results presented in Table 1. The turbidimetric gelation kinetics for UBM and collagen type I gels followed a sigmoidal shape (FIG. 6A). Collagen type I gels at a concentration of 3 mg/ml became more turbid following gelation than UBM-gel at a concentration of 3 mg/ml and 6 mg/ml (FIG. 6A). The lag phase (tlag) and the time required to reach half the final turbidity (t1/2) were greater in the UBM gel (at 3 and 6 mg/ml) than collagen type I (3 mg/ml). In addition, the speed of the turbidimetric gelation kinetics (S) was lower for UBM when compared to collagen type I. There was no change in tlag, t1/2, and S in UBM gels with a change in concentration but there was a change in the maximum turbidity reached.

Turbidimetric kinetics of 1 mg/mL SIS gel also followed a sigmoidal shape (FIG. 7). Whereas UBM measurements were obtained at 405 nm, SIS measurements were obtained at 530 nm. SIS measurements also displayed a decrease in turbidity before maximum turbidity was reached.

Figure 8:
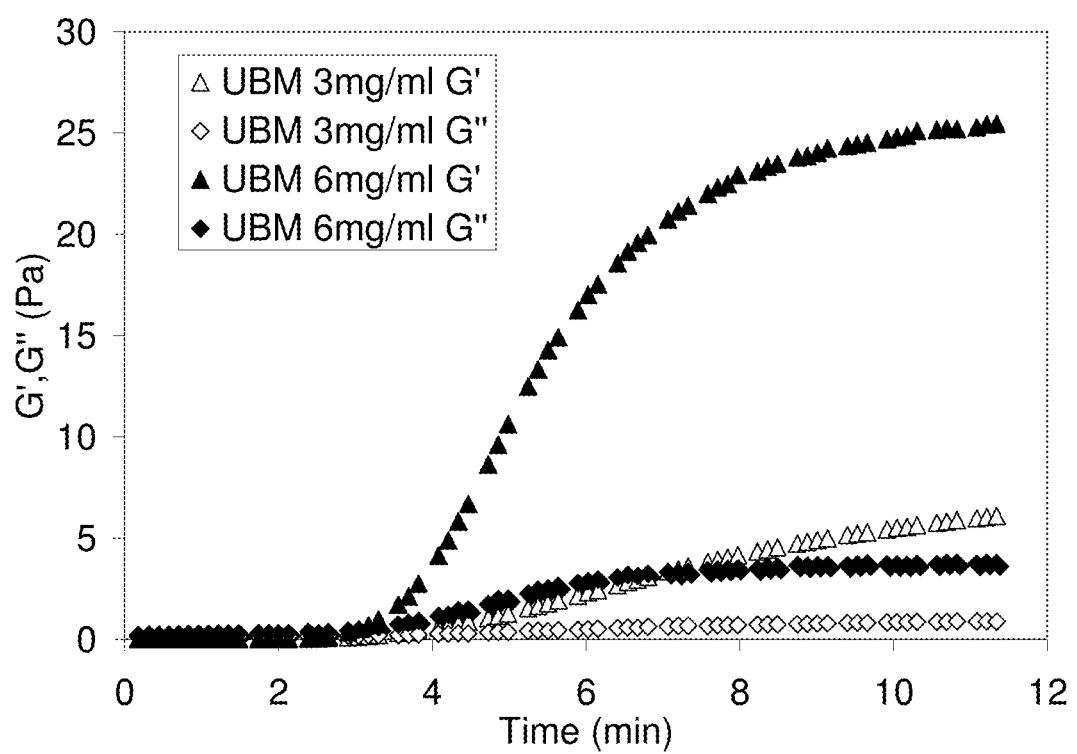
FIG. 8 shows rheological measurements during the gelation of UBM gels, where gelation was determined mechanically by monitoring the oscillatory moduli of the sample at a fixed frequency during gelation. Results are shown of the elastic modulus (G') and of the viscosity modulus (G") for 3 mg/ml UBM gel and for 6 mg/ml UBM gel.
Figure 10:
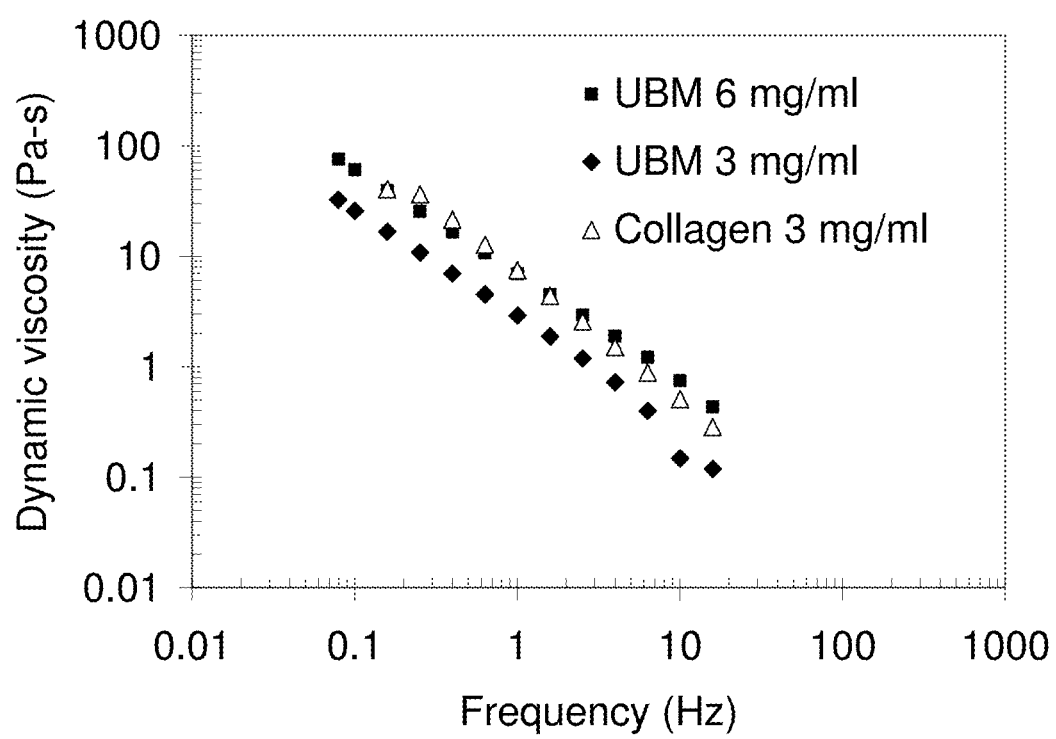
FIG. 10 shows the effect of frequency on the dynamic viscosity of 3 mg/ml Col I gel, 3 mg/ml UBM gel and 6 mg/ml UBM gel (A).

Both the storage modulus (G') and the loss modulus (G") of UBM gels changed over time with a sigmoidal shape after the temperature of the sample was raised from 15° C. to 37° C. (FIG. 8). G' and G" reached a steady state after approximately 8 minutes, suggesting that gelation had occurred. The kinetics of G' and G" were faster than the turbidimetric kinetics. The viscosities of both UBM and collagen type I are shown in FIG. 10 over a frequency range of −0.08-15 Hz and the results are summarized in Table 1.

Figure 9:
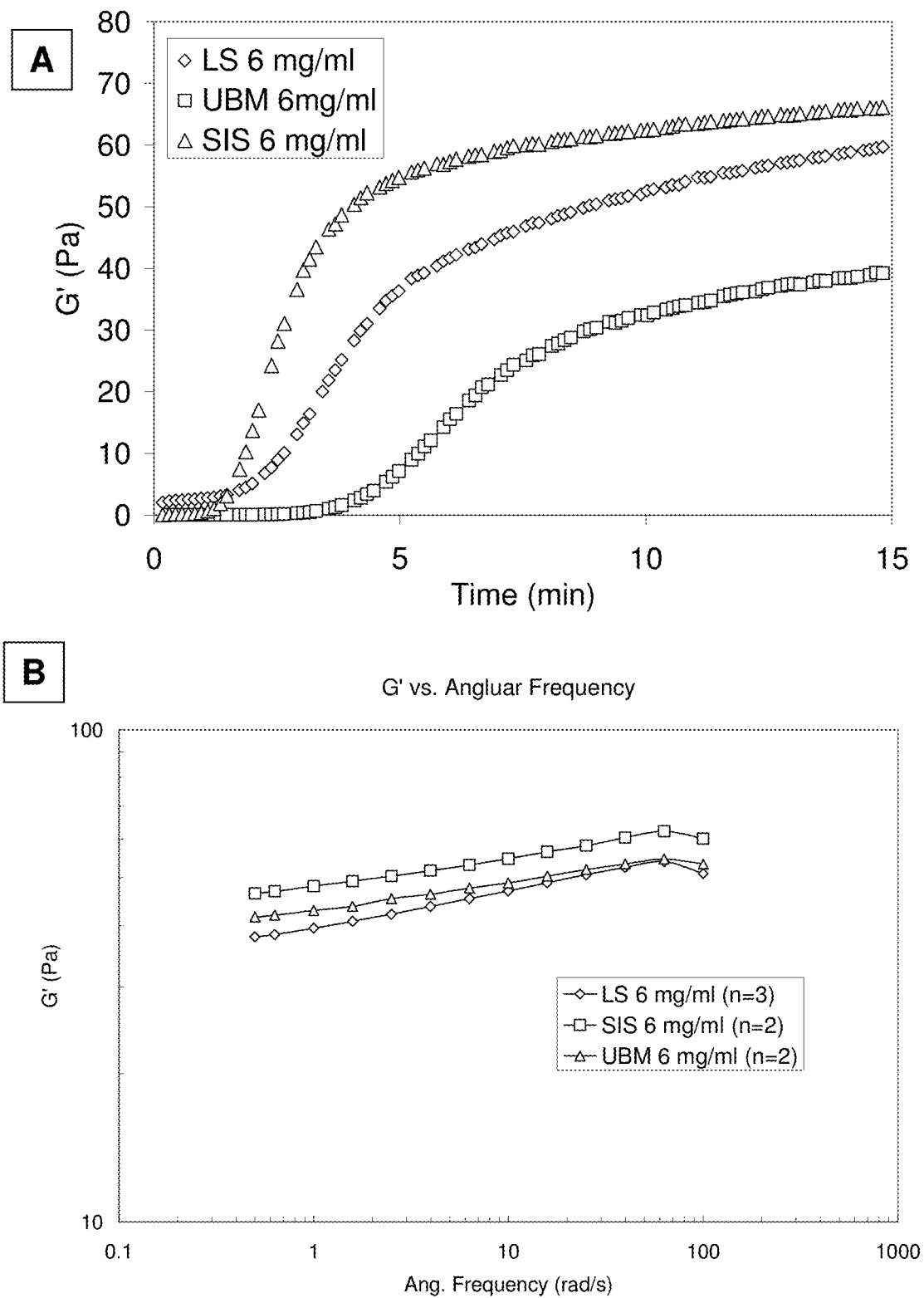
FIG. 9 shows rheological measurements during the gelation of LS (liver stroma) and SIS gels. Gelation kinetics was determined at 5% strain and 1 rad/sec. where results are shown of the elastic modulus (G') for LS, SIS and UBM gels at 6 mg/mL (A). The storage modulus (G') as a function of frequency was also determined for LS, UBM and SIS gels at 6 mg/ml (B).

The storage modulus (G') of LS and SIS gels also changed over time with a sigmoidal shape after the temperature of the sample was raised to 37° C. (FIG. 9A). Kinetics of G' for both LS and SIS gels were faster than kinetics of G' for UBM gels. The storage modulus (G') of LS, SIS and UBM gels were also measured as a function of angular frequency (FIG. 9B).

TABLE 1

Results from the turbidimetric analysis of the UBM gelation kinetics. Data represents mean ± SD. Three samples were tested (n = 3).

| Material | k | $t_{1/2}$ | $t_{lag}$ |
|---|---|---|---|
| Collagen type I 3 mg/ml | 0.20 (0.01)* | 12.2 (1.1)* | 9.7 (0.8)* |
| UBM 3 mg/ml | 0.07 (0.01) | 24.4 (2.4) | 15.8 (2.0) |
| UBM 6 mg/ml | 0.09 (0.04) | 22.4 (4.9) | 14.1 (3.7) |

*$p < 0.05$

In an effort to explore the feasibility of using UBM as an injectable material, multiple trials were performed to test them in an injection setting. ECM powder suspended in saline and UBM gels were tested side by side to see if they could successfully pass through injection needles frequently used in medical procedures such as vocal cord augmentation. These needles had 1 cm long, 25 gauge caliber tips that are attached to 25 cm long, 16 gauge needle shafts. UBM gels easily and consistently passed through these needles. The UBM powder suspension had an upper limit concentration of 10 mg/ml above which the needle would be frequently occluded, making it difficult to determine the actual amount of ECM delivered. This trial showed the feasibility of using the UMB gel as an injectable material (Table 2).

TABLE 2

Comparison of the viscosity of UBM gels with injectable materials commercially available.

| Material | k | n | $r^2$ | Frequency Range [Hz] | REF |
|---|---|---|---|---|---|
| Urinary Bladder Matrix 3 mg/ml | 2.35 | −1.0617 | 0.988 | 0.01-15 | — |
| Urinary Bladder Matrix 6 mg/ml | 5.69 | −0.9547 | 0.999 | 0.01-15 | — |
| Gelatin (Gelfoam) | 149.39 | −0.9030 | 0.997 | 0.01-15 | Chan et al.[a] |
| Zyplast ™ | 99.851 | −0.9145 | 0.998 | 0.01-15 | Chan et al.[a] |
| Zyderm ™ | 66.395 | −0.9154 | 0.998 | 0.01-15 | Chan et al.[a] |
| Zyderm ™ | 12 | −0.860 | 0.977 | 0.01-100 | Klemuk et al.[b] |

TABLE 2-continued

Comparison of the viscosity of UBM gels with injectable materials commercially available.

| Material | k | n | $r^2$ | Frequency Range [Hz] | REF |
|---|---|---|---|---|---|
| Cymetra ® | 19.9 | −0.778 | 0.972 | 0.01-100 | Klemuk et al.[b] |
| Hyaluronic Acid-DTPH | 3.19 | −0.744 | 0.974 | 0.01-100 | Klemuk et al.[b] |
| Human abdominal subcutaneous fat | 23.576 | −0.9508 | 0.994 | 0.01-15 | Chan et al.[b] |
| Polytetrafluoroethylene (PTFE) | 1151.9 | −1.0267 | 0.997 | 0.01-15 | Chan et al.[a] |

[a]Chan RW, et al. Viscosities of implantable biomaterials in vocal fold augmentation surgery. Laryngoscope. 1998 May; 108(5): 725-31.
[b]Klemuk SA, et al. Viscoelastic properties of three vocal-fold injectable biomaterials at low audio frequencies. Laryngoscope. 2004 September; 114(9): 1597-603.

Example 11—Adhesion and Proliferation Assays with Rat Smooth Muscle Cells (rSMCs)

The preparation of UBM has been previously described [Freytes, D O et al, *Biomaterials*, 2004. 25(12): 2353-61]. Briefly, porcine urinary bladders were harvested and the tunica serosa, tunica muscularis externa, tunica submucosa, and most of the tunica muscularis mucosa were mechanically removed. The resulting biomaterial was composed of the basement membrane plus the subjacent tunica propria. T his bi-laminate structure was referred to as urinary bladder matrix or UBM. UBM sheets were disinfected for two hours in a 0.1% (v/v) peracetic acid solution. UBM sheets were either lyophilized or lyophilized and powdered after processing.

One gram of lyophilized UBM powder and 100 mg of pepsin were mixed in 100 mL of 0.01 M HCl and kept at a constant stir for ~48 hrs at room temperature (25° C.). UBM and rat tail collagen type I gels were made by bringing the pH and the ionic strength to physiological range using 1×PBS in a 37° C. incubator. Gel formation kinetics was determined by measuring the absorbance (570 nm) every 2 minutes for ~1.5 hrs. Gels were properly fixed and imaged using scanning electron microscopy (SEM). Equal amounts of each solution were electrophoresed on a gradient 4-20% polyacrylamide gel under reducing conditions (5% 2-Mercaptoethanol). The proteins were visualized with Gel-Code Blue (Bio-Rad), and documented by a Kodak imaging station. Collagen and sulfated glycosaminoglycan (S-GAG) content were determined using the hydroxyproline assay and the Blyscan™ assay kit (Biocolor, Northern Ireland).

Rat smooth muscle cells (rSMCs) were harvested as previously described [Ray J L, Leach R, Herbert J M, Benson M. Isolation of vascular smooth muscle cells from a single murine aorta. Methods Cell Sci. 2001; 23(4):185-8] and expanded in DMEM with low bicarbonate and supplemented with 10% fetal bovine serum (FBS) and 100 U/ml Penicillin/100 μg/ml Streptomycin. The adhesion and proliferation of rSMCs was measured by seeding the surface of 6 mm disks of collagen type I and UBM gels in triplicates. The disks were prepared by adding 100 μl of the appropriate gel (3 mg/ml) onto wells of 96 well plates.

Figure 11:
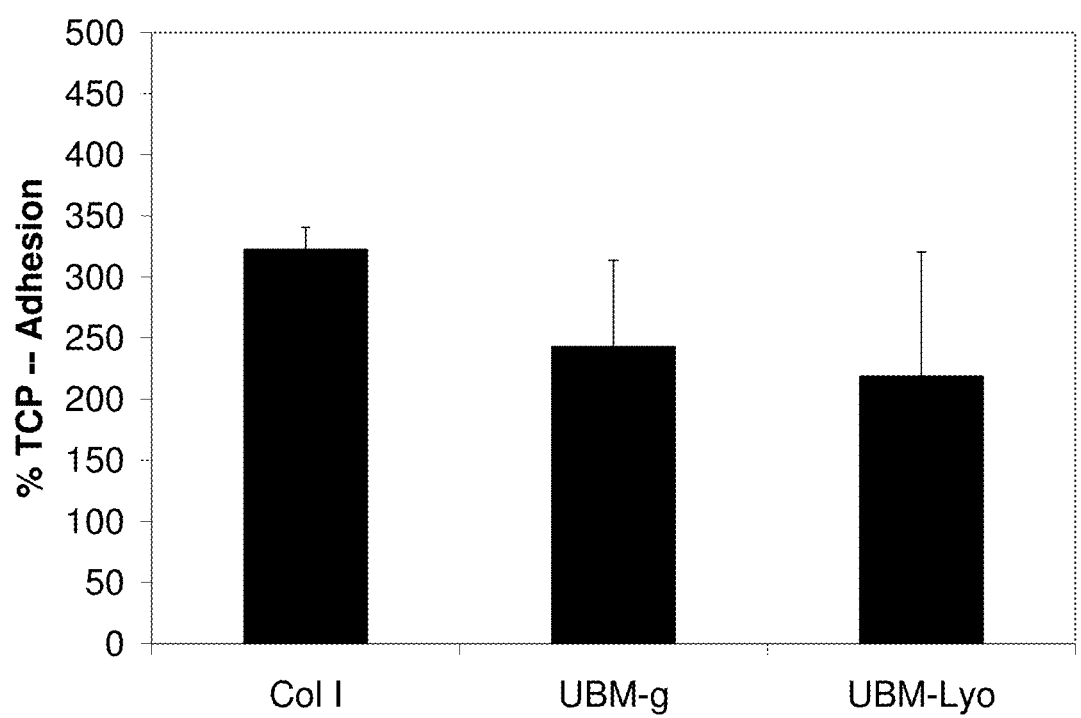
FIG. 11 shows the results of an adhesion assay with rat aortic smooth muscle cells (rSMCs) in culture after 30 minutes, where rSMCs were cultured on Col I gel, UBM gel (UBM-g) and lyophilized UBM sheets (UBM-Lyo). Results are shown for adhesion of rSMCs relative to adhesion of rSMCs on tissue culture plastic (TCP), where the activity of attached cells was determined by a MTT assay (n=3).

Adhesion experiments were performed with rSMCs suspended in serum free DMEM and seeded at a concentration of $4\times10^4$ per well for 30 minutes. Non-adherent cells were removed and the activity of the attached cells was quantified using the MTT assay. The MTT assay is a colorimetric test that measures cell viability by activity of mitochondria within the cells, where increased absorbance at 570 nm relates to increased activity of enzymes within the mitochondria. rSMCs showed similar adhesion on collagen type I (Col I), UBM gels, and lyophilized UBM sheets (FIG. 11).

Figure 12:
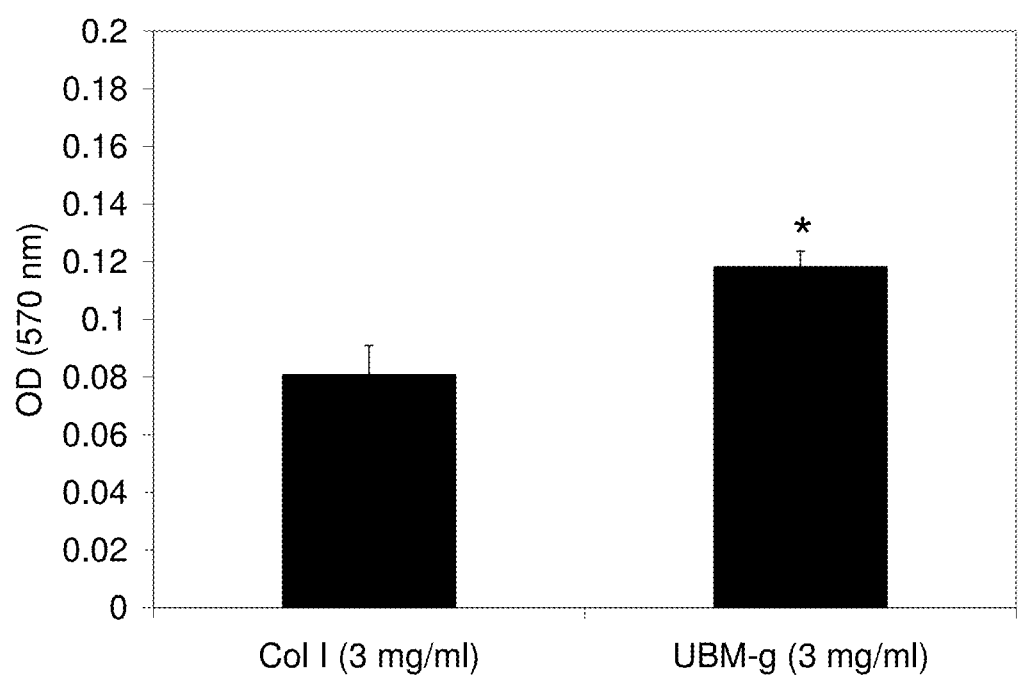
FIG. 12 shows the results of a MTT assay to determine the viability of rSMC cultures after 7 days on either Col I gel or on UBM gel (UBM-g) (n=4, *p<0.05).

Proliferation experiments were performed with rSMCs at three different concentrations (1, 2 and $4\times10^4$ cells per well), and the activity of the cells was determined using the MTT assay by following the manufacturer's instructions. rSMCs successfully adhered to UBM gels and were able to grow for 48 hours with a slight increase in cell activity when compared to cells grown on collagen type I (Table 3). rSMCs cultured for one week also showed an increase in mitochondrial activity on UBM gels when compared to the activity on collagen type I gels (see FIG. 12).

TABLE 3

Results form the proliferation and adhesion assays using primary rat aortic endothelial cells. Data represents mean ± SD. Three samples were tested (n = 3).

| Assay | Initial Cell Number | % of Cellular Activity when Compared to Collagen Type I |
|---|---|---|
| 48 hrs proliferation | $1 \times 10^4$ | 124 (12) |
| | $2 \times 10^4$ | 111 (13) |
| | $4 \times 10^4$ | 119 (7) |
| 30 min adhesion | $4 \times 10^4$ | 73 (29) |

Figure 13:
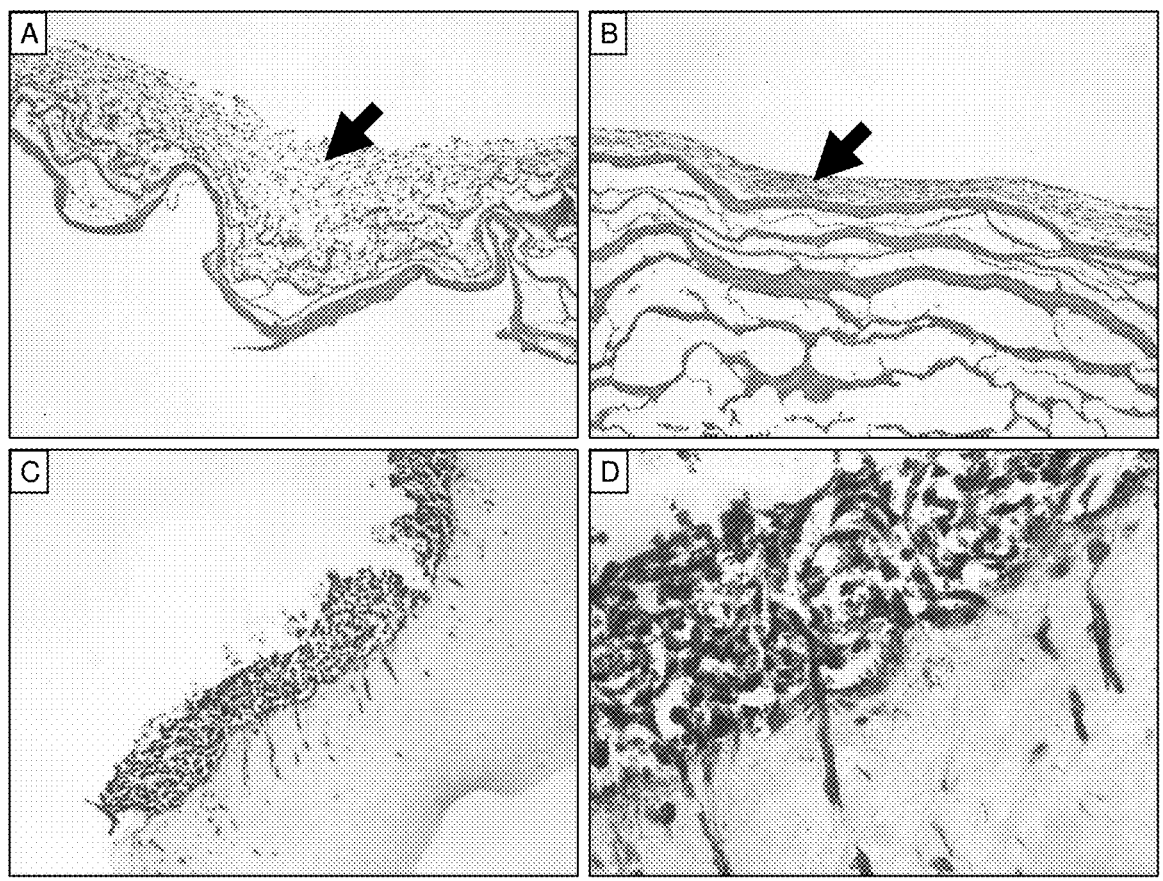
FIG. 13 shows histological images of rSMC cultures after 7 days. Images are shown for rSMCs (shown by arrows) at 10× on the abluminal (A) and luminal (B) sides of the UBM-Lyo sheets, where samples were fixed and stained with H & E. Images are also shown for cultures at 10× (C) and at 20× (D) on UBM gels, where samples were fixed and stained with Masson's trichrome.
Figure 14:
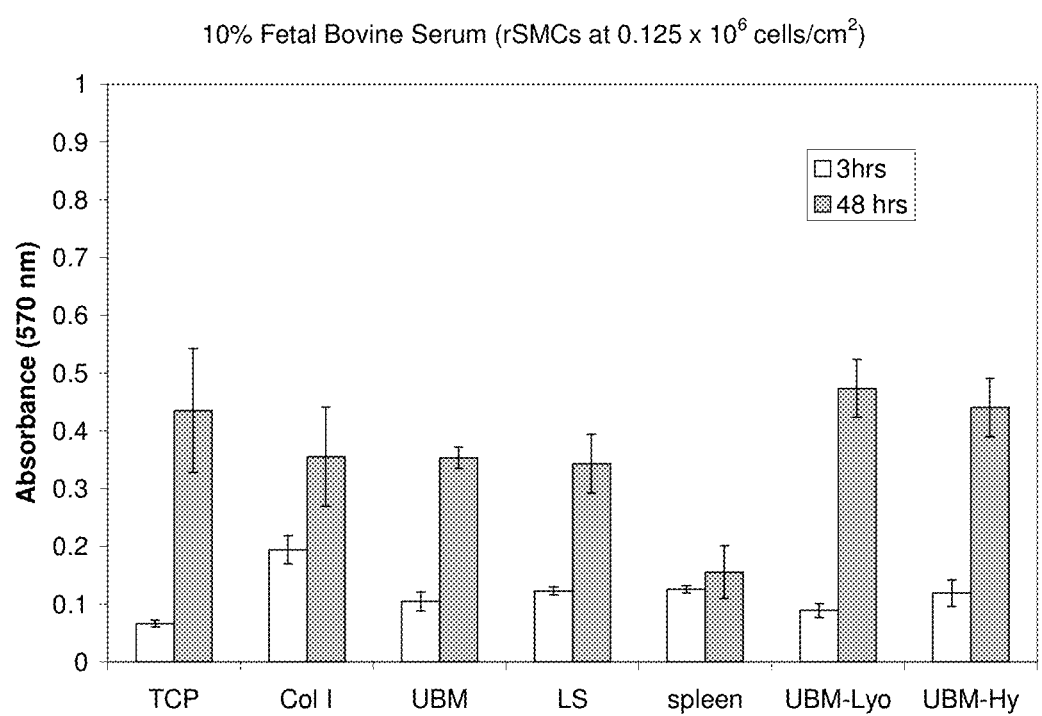
FIG. 14 shows the results of a MTT assay to determine the viability of rSMC cultures after 3 hours and after 48 hours on different substrates: tissue culture plate (TCP), Col I (collagen type I gel), UBM (Urinary bladder matrix gel), LS (porcine liver stroma gel), spleen (spleen ECM gel), UBM-Lyo (lyophilized UBM sheet) and UBM-Hy (hydrated UBM sheets). All gels were at 6 mg/ml.

Growth of rSMCs on collagen type I gels, UBM gels, and UBM lyophilized sheets was also examined histologically. Disks of UBM gel were made using a stainless steel ring (1.5 cm in diameter) as a mold. rSMCs were seeded on the top surface of the gel at a density of $0.5\times10^6$ cells/cm². Media was changed every other day and the cells were allowed to grow for 10 days. The samples where then fixed with 10% buffered formalin and stained using H&E or Masson's Trichrome stain. rSMCs formed a confluent multilayer after the 7-10 day incubation period on both UBM gels and UBM lyophilized sheets (FIG. 13). Contraction of the UBM and collagen type I gels was observed which could suggest a change of the rSMCs from a proliferative state to a contractile state when seeded on the gels, which shows that cell-matrix interactions and traction forces were formed during in vitro culture Cell viability was also measured over a period of 48 hours on different types of ECM-derived gels. rSMCs were seeded at $0.125\times10^6$ cells/cm² in triplicates on the surface of different substrates and the MTT assay used to determine cell viability at 3 and 48 hours following seeding (FIG. 14). TCP=Tissue Culture Plate; Col I=Purified Collagen Type I Gel; UBM=Urinary Bladder Matrix Gel; LS=Porcine Liver Stroma Gel; Spleen=Spleen ECM Gel; UBM-Lyo=Lyophilized UBM sheet; and UBM-Hy=Hydrated UBM sheets. All gels were at a 6 mg/ml concentration.

Preliminary implantation of 6 mg/ml UBM gels on a subcutaneous pocket of a rat showed complete degradation of the scaffold after 14 days with no signs of inflammation (unpublished results). Together, these data show the potential cytocompatibility of the UBM gels but further in vivo testing is required.

Example 12—Chemotaxis Assay with Human Aortic Endothelial Cells

Figure 15:
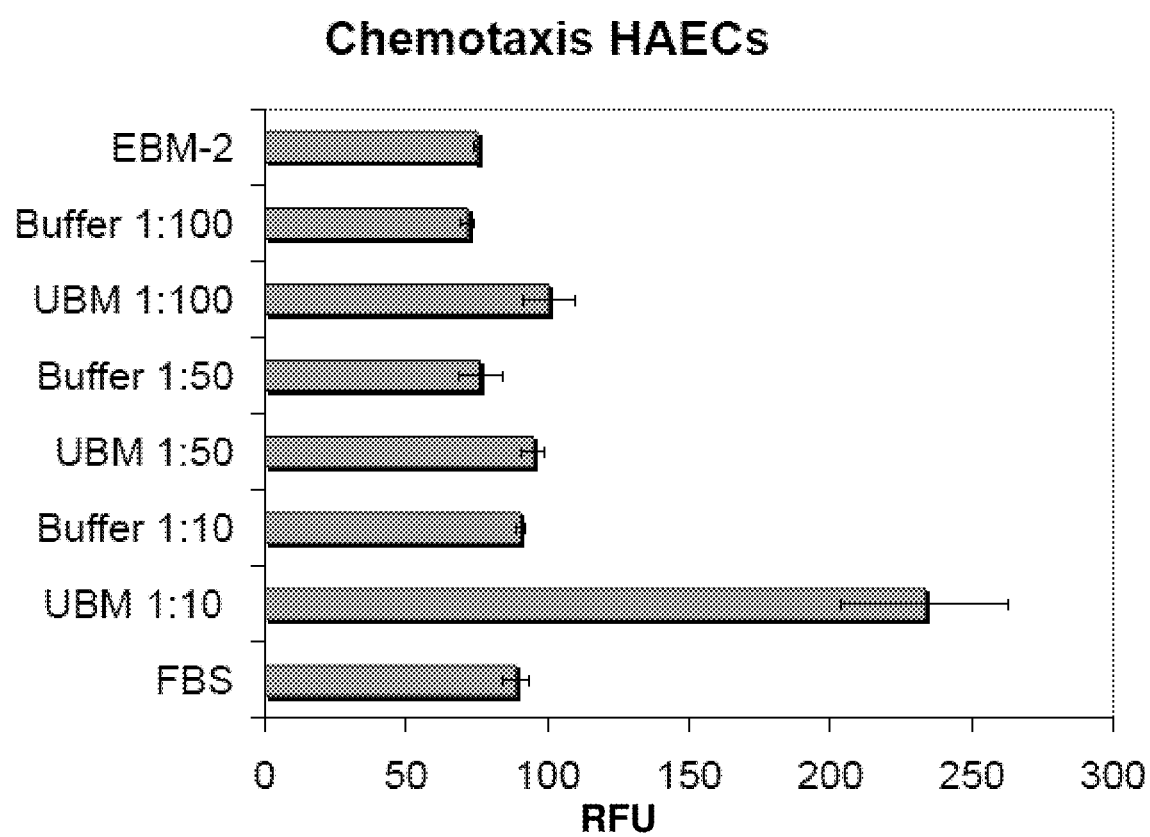
FIG. 15 shows the results of a chemotaxis assay of human aortic endothelial cells (HAECs) for different solutions: dilutions of digest solution of UBM with a solution containing acid and pepsin (UBM), dilutions of EBM-2 media with a solution containing acid and pepsin (Buffer), endothelial basal cell medium (EBM-2) and fetal bovine serum (FBS). Chemotaxis was assessed using CytoSelect™ 96-well Cell Migration Assay, where relative fluorescence units (RFU) correlated to the number of migratory cells that achieved chemotaxis.

The solubilized UBM also retains its bioactivity such as chemoattractant properties, where human aortic endothelial cells (HAECs) migrated towards a UBM digest solution more than towards a solution containing pepsin alone (FIG. 15, comparing data from "Buffer 1:10" to "UBM 1:10").

Chemotaxis assay was assessed using CytoSelect™ 96-well Cell Migration Assay following the manufacturer's instructions. Briefly, a membrane with a small pore size discriminates between migratory and non-migratory cells. Migratory cells extend protrusions towards the chemoattractants on the other side of the membrane and pass through the pores. These migratory cells are dissociated from the membrane and detected by fluorescence with CyQuant® GR Dye (Invitrogen), which binds to cellular nucleic acid. Therefore, increased relative fluorescence units (RFU) correlated to a higher number of migratory cells that achieved chemotaxis through the membrane.

Figure 16:
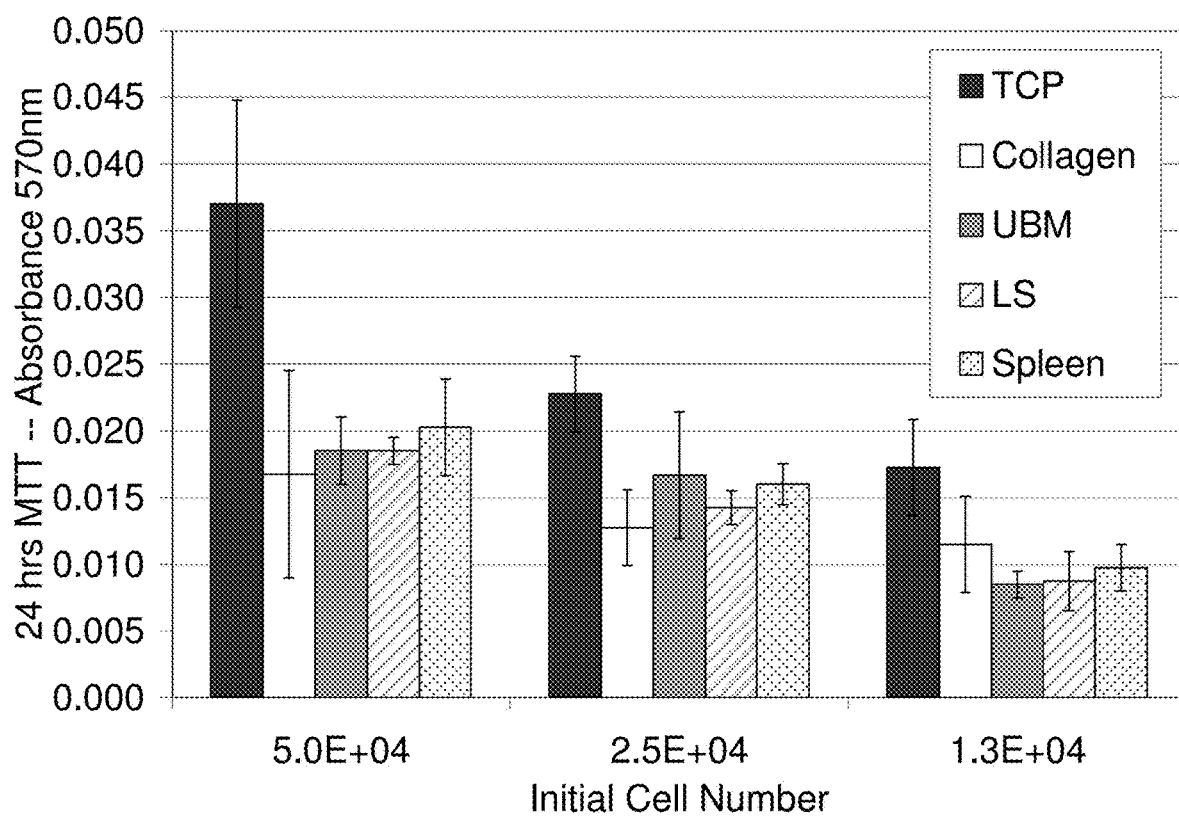
FIG. 16 shows the results of a MTT assay to determine the viability of human microvascular endothelial cells on different substrates: tissue culture plate (TCP), Collagen (collagen type I gel), UBM (Urinary bladder matrix gel), LS (porcine liver stroma gel), and spleen (spleen ECM gel). All gels were at 6 mg/ml and cells were seeded in triplicates (n=3).

Example 13—Adhesion and Proliferation Assay with Human Aortic Endothelial Cells Human microvascular endothelial cells (at the mentioned Initial Cell Number per well) were seeded in triplicates on the surface of different substrates and the MTT assay used to determine cell viability (FIG. 16). TCP=Tissue Culture Plate; Collagen=Purified Collagen Type I, UBM=Urinary Bladder Matrix Gel; LS=Porcine Liver Stroma Gel; Spleen=Spleen ECM Gel. All gels were at a 6 mg/ml concentration.

Example 14—Hybrid Inorganic/ECM Scaffold

Restoration of joint kinematics after limb amputation and replacement with a prosthesis is limited due to the inability to attach existing musculature to the prosthesis via boney insertion of tendons [Higuera, C. A., et al.: J Orthop Res. 1091-9 (23) 2005]. Although a variety of porous titanium and tantalum alloys have been successful at promoting bone ingrowth, there are no alternatives to promote the ingrowth of fibrocartilaginous tissue that restores a ligament or tendon insertion site. Recently, porous tantalum scaffolds have been investigated for their ability to promote ingrowth of a vascularized fibrous tissue with promising mechanical strength [Hacking, S. A., et al.: J Biomed Mater Res, 631-8 (52) 2000]. Naturally derived extracellular matrix (ECM) scaffolds from the porcine small intestine and urinary bladder (UBM) have also been shown to form well organized tendon, ligament, cartilage, and bone, as well as strong boney insertion sites with good mechanical strength [Badylak, S. F.: Transpl Immunol. 367-77 (12) 2004; Dejardin, L. M., et al.: AJSM. 175-84 (29) 2001]. It is reasonable to expect that a porous tantalum or titanium scaffold with an ECM embedded within the pores may improve the ingrowth of soft tissue into the metal surface and promote the formation of fibrocartilaginous tissue. The goal of the current study was to determine the feasibility of coating a porous titanium scaffold with an ECM gel for the eventual application of ligament or tendon insertion repair.

UBM powder was produced as described previously [Freytes, D O et al, Biomaterials, 2004. 25(12): 2353-61]. A UBM gel digest was prepared by mixing one gram of lyophilized UBM powder with 100 mg of pepsin in 100 mL of 0.01 M HCl under constant stirring for −48 hrs at room temperature. UBM gel polymerization was initiated by bringing the pH and the ionic strength to physiological range using PBS at 37° C. Complete polymerization of the gel occurred within 30 min. The porous metal scaffolds were cleaned with acetone, methanol, and water, and passivated with 20-45% nitric acid.

The contact angles between the UBM gel digest (before [10 mg/ml] and after physiologic activation [6 mg/ml]) and sheets of CP Ti or Ti 6Al 4V were measured. One ml of the digest was added to each surface and a digital photograph was taken for subsequent angle determination.

Two methods tested for ability to promote penetration of the polymerized UBM gel into either CP titanium fiber mesh or CP titanium sintered beads. The entire surface of each porous metal scaffold was covered with activated UBM gel for 5 minutes. For half of the scaffolds, the gel was permitted to penetrate under static conditions, while in the other half of the samples penetration took place using ultrasonication. Dye was added to visualize the gel.

To verify the presence of UBM gel within the porous titanium scaffolds and to better understand the interaction between the UBM gel and the metal, specimens were prepared for environmental scanning electron microscopy (ESEM). Since the samples were able to be visualized with ESEM while still in the hydrated condition, the interactions between the titanium scaffold and the UBM gel were able to be determined without disruption of the ECM by dehydration.

Figure 17:
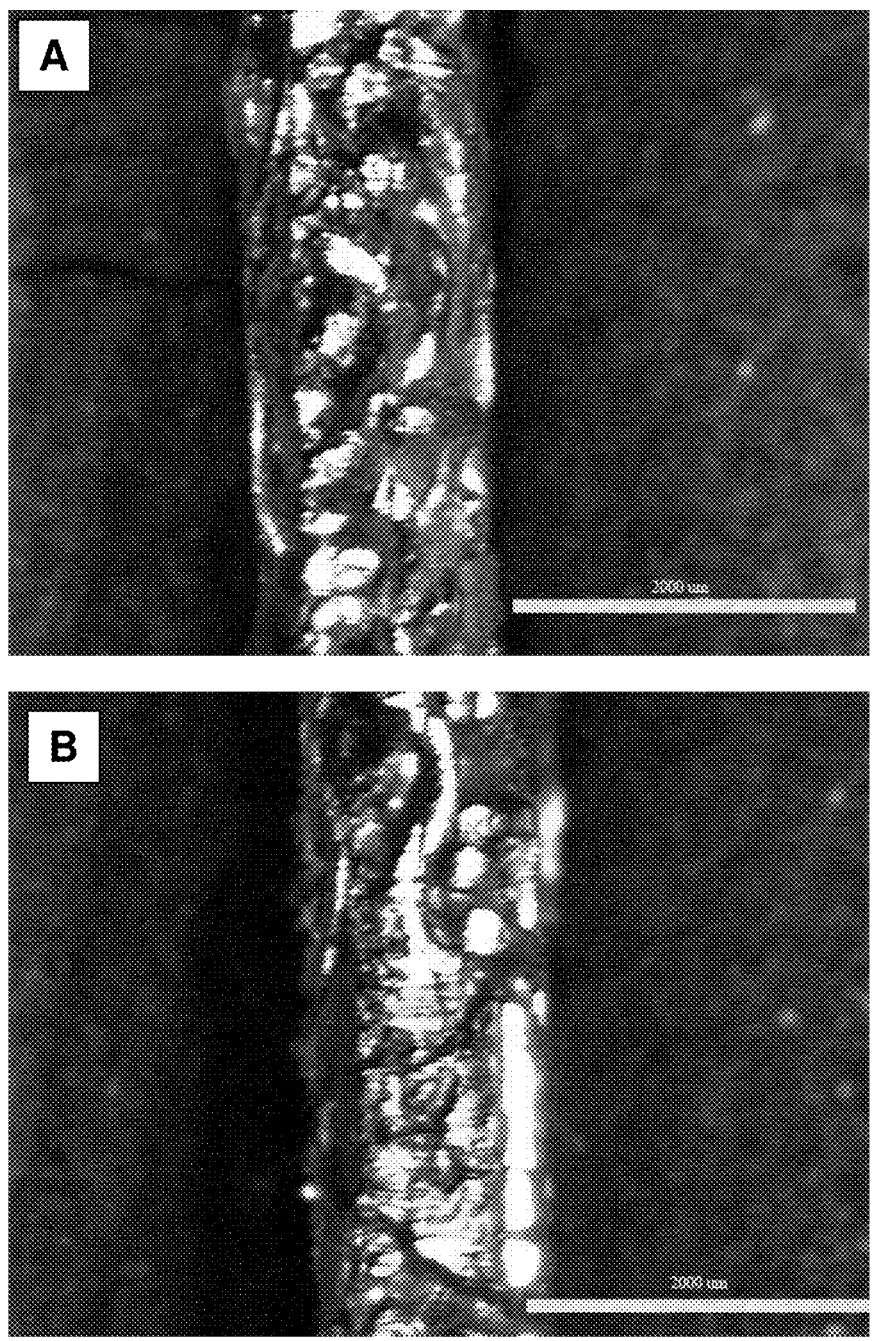
FIG. 17 shows digital photographs of a porous titanium fiber penetrated with UBM gel (stained in turquoise), where the fiber was treated without (A) and with (B) ultrasonication. Scale bars are 2000 am.
Figure 18:
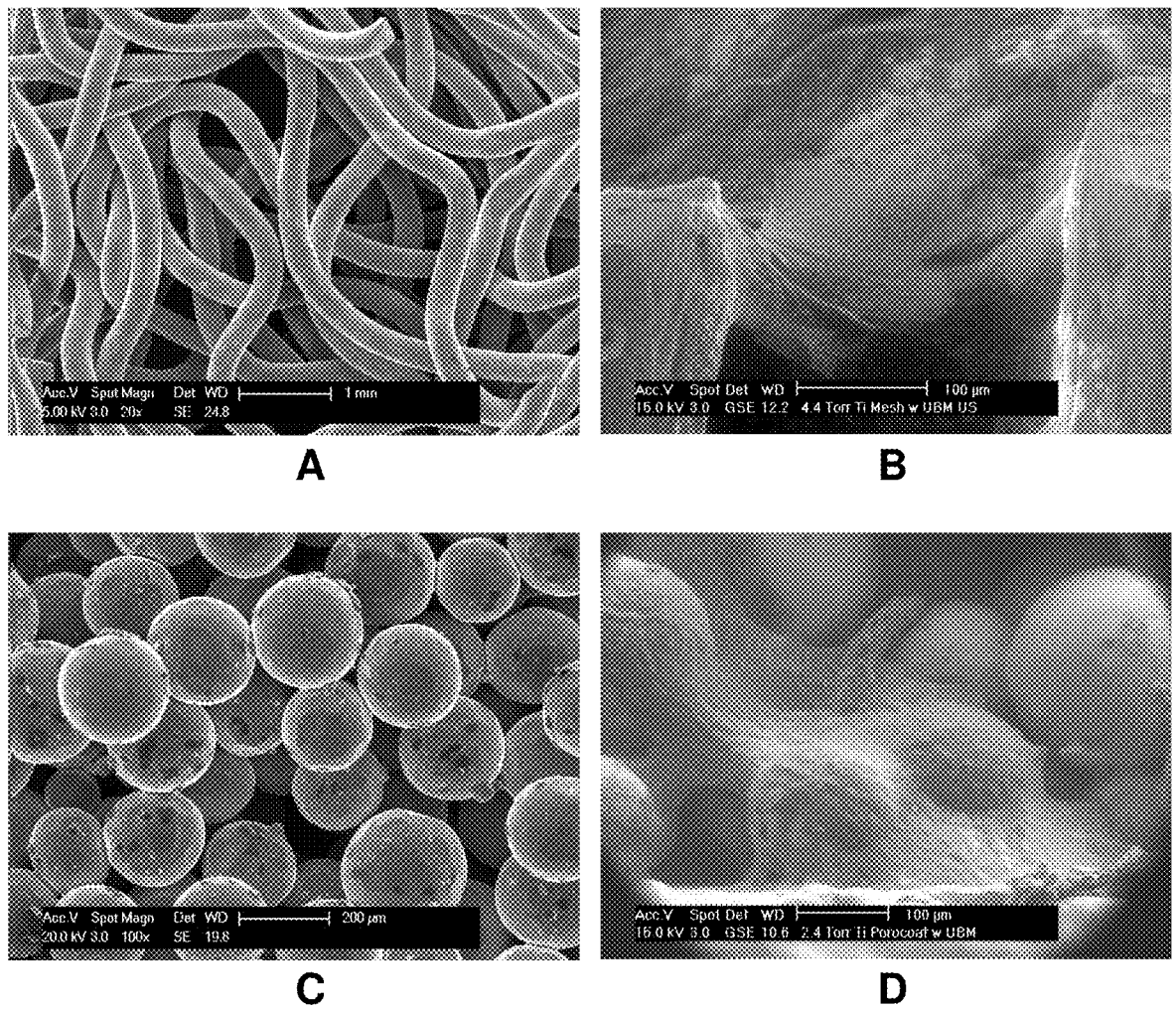
FIG. 18 shows SEM images of porous metal scaffolds and ESEM (environmental scanning electron microscopy) images of hybrid extracellular matrix (ECM)/porous metal scaffolds. SEM images are shown of a porous metal scaffold containing Ti6Al4V wires in a fiber mesh (A) or containing sintered commercially pure titanium (CP Ti) beads (C). ESEM images are shown of the hybrid ECM/porous metal scaffold, where UBM gel coats both the Ti6Al4V wires (B) and the CP Ti beads (D) after exposure to ultrasonication.

Both the UBM gel digest and the activated UBM gel wet the surface of the CP Ti and Ti 6Al 4V well (Table 4). Therefore, the porous metal should not exclude the ECM. Based on these results, subsequent experiments focused on the activated gel. The UBM gel was able to penetrate half way through the thickness of each porous metal scaffold in the static condition. With the addition of ultrasonication, pores were infiltrated through the entire thickness of the scaffold (FIG. 17). Examination of the hybrid scaffolds with ESEM showed excellent penetration within and coverage of the porous titanium (FIG. 18).

It is possible to create a hybrid ECM/porous metal scaffold using UBM gel and a porous titanium scaffold. Future studies will evaluate whether these scaffolds can support cell growth in vitro and promote connective tissue ingrowth in vivo. The eventual goal of this effort is to develop a scaffold that will promote ingrowth of soft tissue into the metal to serve as an insertion site for ligaments and tendons.

TABLE 4

Contact angle for UBM material on titanium alloys (Mean ± SD)

| Type of Metal | UBM digest | UBM gel |
|---|---|---|
| CP Ti | 46.8 ± 1.3 | 27.0 ± 4.0 |
| Ti6Al4V | 38.2 ± 4.8 | 41.3 ± 1.6 |

We claim:
1. A composition comprising:
an acidic solution comprising an acid protease and solubilized, non-dialyzed, non-crosslinked extracellular matrix from a tissue selected from the group consisting of heart, pancreas, liver, ovary, spleen, and urinary bladder removed of submucosa;

wherein, the acidic solution, when neutralized, forms a gel at a temperature greater than 25° C.

2. The composition of claim 1, wherein the ECM is from heart tissue.

3. The composition of claim 1, wherein the ECM is from liver tissue.

4. The composition of claim 1, wherein the acid protease is pepsin.

5. The composition of claim 1, wherein the solution is frozen.

6. The composition of claim 1, wherein the solution has a pH of about 2.

7. A composition comprising:
a hydrogel comprising solubilized, non-dialyzed, non-crosslinked extracellular matrix (ECM) and an acid protease, the hydrogel having a pH in the range of 7.2 to 7.8.

8. The composition of claim 7, wherein the acid protease is pepsin.

9. The composition of claim 7, wherein the ECM is derived from a tissue selected from intestine, urinary bladder, liver, esophagus, pancreas, dermis, heart, ovary, or spleen.

10. The composition of claim 9, wherein the ECM is derived from heart.

11. The composition of claim 9, wherein the ECM is derived from liver.

12. The composition of claim 7, wherein the pH is in the range of 7.2 to 7.4.

13. A method of preparing an extracellular matrix-derived gel comprising:
neutralizing an acidic solution comprising solubilized, digested, non-dialyzed, non-crosslinked extracellular matrix (ECM) and an acid protease to produce a neutralized solution, wherein the neutralized solution produces a hydrogel at a temperature greater than 25° C.

14. The method of claim 13, wherein the neutralized solution has a pH in the range of 7.2 to 7.8.

15. The method of claim 13, wherein the acid protease is pepsin.

16. The method of claim 13, wherein the hydrogel forms after 40 minutes at 37° C.

17. The method of claim 13, wherein the ECM is derived from a tissue selected from intestine, urinary bladder, liver, esophagus, pancreas, dermis, heart, ovary, or spleen.

18. A method of preparing a gelable extracellular matrix composition comprising:
solubilizing non-dialyzed, non-crosslinked extracellular matrix (ECM) in an acidic solution with an acid protease to produce an acidic solution of solubilized, digested, non-dialyzed, non-crosslinked ECM and the acid protease;
wherein, upon neutralizing the acidic solution to produce a neutralized solution having a pH of between 7.2 to 7.8, the solution forms a gel at a temperature greater than 25° C.

19. The method of claim 18, wherein the ECM is from a tissue selected from the group consisting of intestine, urinary bladder, liver, esophagus, pancreas, dermis, heart, ovary, and spleen.

20. The method of claim 19, wherein the ECM is from heart tissue.

21. The method of claim 19, wherein the ECM is from liver tissue.

22. The method of claim 18, wherein the acid protease is pepsin.

23. The method of claim 18, wherein the ECM is lyophilized or dried, and then comminuted prior to solubilizing in the acidic solution.

24. The method of claim 18, wherein the ECM is solubilized by stirring in the acidic solution at room temperature.

25. The method of claim 18, wherein the pH of the acidic solution is about 2.

* * * * *